(12) United States Patent
Call et al.

(10) Patent No.: US 8,047,053 B2
(45) Date of Patent: Nov. 1, 2011

(54) MAIL PARCEL SCREENING USING MULTIPLE DETECTION TECHNOLOGIES

(75) Inventors: Charles J. Call, Albuquerque, NM (US); Carl Chipman, Stillwater, OK (US); Greg Frye-Mason, Cedar Crest, NM (US); Riney Bennett, Los Alamos, NM (US)

(73) Assignee: ICX Technologies, Inc., Arlington, VA (US)

( * ) Notice: Subject to any disclaimer, the term of this patent is extended or adjusted under 35 U.S.C. 154(b) by 845 days.

(21) Appl. No.: 12/118,594

(22) Filed: May 9, 2008

(65) Prior Publication Data
US 2009/0248319 A1    Oct. 1, 2009

Related U.S. Application Data

(60) Provisional application No. 60/916,972, filed on May 9, 2007.

(51) Int. Cl.
*G01N 1/22* (2006.01)
*B07C 1/04* (2006.01)

(52) U.S. Cl. .................. 73/28.01; 73/31.01; 73/31.03; 73/864.33

(58) Field of Classification Search ............... 73/23.2, 73/28.01, 31.03–31.04, 31.07, 863.21–863.23, 73/863.71, 864.33; 209/606, 655, 659, 663; 340/540, 632; 435/287.1, 587.1; 705/402, 705/410
See application file for complete search history.

(56) References Cited

U.S. PATENT DOCUMENTS

| | | | |
|---|---|---|---|
| 877,460 A | 1/1908 | Brunner et al. | |
| 902,958 A | 11/1908 | Galusha | |
| 906,038 A | 12/1908 | Lauder | |
| 1,603,878 A | 10/1926 | Smith | |
| 1,662,870 A | 3/1928 | Stancliffe | |
| 1,749,920 A | 3/1930 | Modave | |
| 1,807,378 A | 5/1931 | Budil | |
| 1,825,274 A | 9/1931 | Leach | |
| 2,937,780 A | 5/1960 | Beckwith | 220/560.14 |
| 2,939,545 A | 6/1960 | Silverman | |
| 3,001,914 A | 9/1961 | Andersen | 435/30 |
| 3,291,282 A * | 12/1966 | Pedagno | 198/550.4 |
| 3,469,934 A | 9/1969 | Bocard et al. | |

(Continued)

FOREIGN PATENT DOCUMENTS

JP    59196713    11/1984

(Continued)

OTHER PUBLICATIONS de la Mora, J.F., "Aerodynamic Focusing of Particles and Heavy Molecules: First Annual Report," *NTIS*: 16pp., Feb. 16, 1988.

(Continued)

*Primary Examiner* — David A. Rogers
(74) *Attorney, Agent, or Firm* — McAfee & Taft

(57) ABSTRACT

Various screening systems are disclosed, including a system including a radiation detection component, a toxic chemical detection component, a toxic chemical agent sampling component, a bio-threat detection component, a puffer-based bio-threat sampling component, an explosive detection component, and an X-ray based imager, such that it automatically screens mail for the presence of multiple threat agents, such as chemical, biological, radiological, nuclear and explosive threats. An automated sample arm collects a sample when a sampling substrate contacts a portion of the item of mail while there is relative motion between the automated sample arm and the item of mail. The sample is conveyed to a detector and the sampling substrate is regenerated by heating it.

29 Claims, 16 Drawing Sheets

U.S. PATENT DOCUMENTS

| | | | | |
|---|---|---|---|---|
| 3,518,815 | A | 7/1970 | McFarland et al. | 73/863.22 |
| 3,572,128 | A | 3/1971 | Hemeon | 73/863.24 |
| 3,633,405 | A | 1/1972 | Noll | 73/28.06 |
| 3,693,457 | A | 9/1972 | Pilat | 73/432 |
| 3,754,868 | A | 8/1973 | Witz et al. | 23/254 |
| 3,760,630 | A | 9/1973 | Brumbaugh | 73/28.05 |
| 3,891,550 | A | 6/1975 | Gray et al. | 210/67 |
| 3,901,798 | A | 8/1975 | Peterson | 209/143 |
| 3,922,905 | A | 12/1975 | Roth | 73/28.04 |
| 3,932,151 | A | 1/1976 | Lau | 55/229 |
| 3,942,357 | A | 3/1976 | Jenkins | 73/31.07 |
| 3,970,428 | A | 7/1976 | Barringer | 23/230 |
| 3,972,226 | A | 8/1976 | Rountree et al. | 73/28.05 |
| 3,983,743 | A | 10/1976 | Olin et al. | 73/28 |
| 3,997,297 | A | 12/1976 | Jenkins et al. | 23/232 E |
| 3,998,101 | A * | 12/1976 | Bradshaw et al. | 73/864 |
| 4,111,049 | A | 9/1978 | Lerner et al. | 73/421.5 R |
| 4,133,202 | A | 1/1979 | Marple | 73/28 |
| 4,136,780 | A * | 1/1979 | Hunter et al. | 209/539 |
| 4,149,622 | A * | 4/1979 | Bradshaw et al. | 198/444 |
| 4,301,002 | A | 11/1981 | Loo | 209/143 |
| 4,321,822 | A | 3/1982 | Marple et al. | 73/28 |
| 4,350,571 | A | 9/1982 | Erickson | 203/21 |
| 4,387,603 | A | 6/1983 | Nelson | 73/863.22 |
| 4,415,265 | A | 11/1983 | Campillo et al. | 356/338 |
| 4,452,068 | A | 6/1984 | Loo | 73/28 |
| 4,473,384 | A | 9/1984 | Lefkowitz | 55/290 |
| 4,580,440 | A | 4/1986 | Reid et al. | 73/23 |
| 4,590,792 | A | 5/1986 | Chiang | 73/28 |
| 4,640,140 | A | 2/1987 | Burghoffer et al. | 73/863.22 |
| 4,670,135 | A | 6/1987 | Marple et al. | 209/143 |
| 4,689,052 | A | 8/1987 | Ogren et al. | 55/17 |
| 4,697,462 | A | 10/1987 | Daube, Jr. et al. | 73/863.21 |
| 4,742,009 | A | 5/1988 | Beverly et al. | 436/57 |
| 4,764,186 | A | 8/1988 | Langer | 95/268 |
| 4,767,524 | A | 8/1988 | Yeh et al. | 209/143 |
| 4,790,860 | A | 12/1988 | Sexton | 55/59 |
| 4,820,920 | A | 4/1989 | Bather | 250/282 |
| 4,872,972 | A | 10/1989 | Wakabayashi et al. | 209/143 |
| 4,877,430 | A | 10/1989 | Gutermuth | 55/269 |
| 4,877,516 | A | 10/1989 | Schram | 209/155 |
| 4,941,899 | A | 7/1990 | Liu | 73/863.23 |
| 4,942,297 | A | 7/1990 | Johnson et al. | 250/304 |
| 4,961,966 | A | 10/1990 | Stevens et al. | 427/299 |
| 4,972,957 | A | 11/1990 | Liu et al. | 209/143 |
| 4,987,286 | A | 1/1991 | Allen | 219/121.68 |
| 4,990,740 | A | 2/1991 | Meyer | 219/121.52 |
| 5,039,490 | A | 8/1991 | Marsoner et al. | 422/82.01 |
| 5,040,424 | A | 8/1991 | Marple et al. | 73/863.23 |
| 5,063,164 | A | 11/1991 | Goldstein | 436/169 |
| 5,128,539 | A | 7/1992 | Rodgers et al. | 250/255 |
| 5,144,175 | A | 9/1992 | Craggs | 310/63 |
| 5,162,810 | A | 11/1992 | Onisawa et al. | 343/912 |
| 5,201,231 | A | 4/1993 | Smith | 73/863.22 |
| 5,254,861 | A | 10/1993 | Carpenter et al. | 250/573 |
| 5,294,410 | A | 3/1994 | White | 422/171 |
| 5,299,141 | A | 3/1994 | Hungerford et al. | 364/510 |
| 5,304,125 | A | 4/1994 | Leith | 604/57 |
| 5,318,609 | A | 6/1994 | Kittler | 55/443 |
| 5,326,537 | A | 7/1994 | Cleary | 422/173 |
| 5,332,550 | A | 7/1994 | Booker | 422/83 |
| 5,412,975 | A | 5/1995 | Raabe et al. | 73/28.04 |
| 5,421,214 | A | 6/1995 | Burgdorfer | 73/863.22 |
| 5,425,263 | A | 6/1995 | Davies et al. | 73/28.05 |
| 5,425,802 | A | 6/1995 | Burton et al. | 95/32 |
| 5,428,222 | A | 6/1995 | Alexay | 250/343 |
| 5,437,198 | A | 8/1995 | John | 73/863.22 |
| 5,461,473 | A | 10/1995 | Pratt et al. | 356/141.3 |
| H1499 | H | 11/1995 | Vance | 55/446 |
| 5,472,645 | A | 12/1995 | Rock et al. | 261/79.1 |
| 5,498,271 | A | 3/1996 | Marple et al. | 55/321 |
| 5,512,216 | A | 4/1996 | Rock et al. | 261/79.1 |
| 5,518,697 | A | 5/1996 | Dalla Betta et al. | 422/173 |
| 5,533,406 | A | 7/1996 | Geise | 73/863.22 |
| 5,534,328 | A | 7/1996 | Ashmead | 428/166 |
| 5,552,051 | A | 9/1996 | Wang et al. | 210/604 |
| 5,553,795 | A | 9/1996 | Tsai et al. | 241/40 |
| 5,584,557 | A | 12/1996 | Alexay | 362/32 |
| 5,585,575 | A | 12/1996 | Corrigan et al. | 73/863.71 |
| 5,658,537 | A | 8/1997 | Dugan | 422/191 |
| 5,669,811 | A | 9/1997 | Zaniewski | 454/16 |
| 5,681,752 | A | 10/1997 | Prather | 436/173 |
| 5,693,895 | A | 12/1997 | Baxter | 73/863.22 |
| 5,760,314 | A | 6/1998 | Bromberg et al. | 73/863.21 |
| 5,776,754 | A | 7/1998 | Caldwell | 435/240.2 |
| 5,786,894 | A | 7/1998 | Shields et al. | 356/338 |
| 5,788,741 | A | 8/1998 | Burton et al. | 95/32 |
| 5,811,062 | A | 9/1998 | Wegeng et al. | 422/129 |
| 5,858,043 | A | 1/1999 | Geise | 55/462 |
| 5,859,362 | A * | 1/1999 | Neudorfl et al. | 73/23.2 |
| 5,859,375 | A | 1/1999 | Danylewych-May et al. | 73/864.71 |
| 5,914,091 | A | 6/1999 | Holst et al. | 422/173 |
| 5,925,960 | A | 7/1999 | Hayes | 310/211 |
| 5,932,795 | A | 8/1999 | Koutrakis et al. | 73/28.01 |
| 5,935,339 | A | 8/1999 | Henderson et al. | 134/1 |
| 5,942,699 | A | 8/1999 | Ornath et al. | 73/863.21 |
| 5,949,001 | A | 9/1999 | Willeke | 73/865.5 |
| 5,967,332 | A | 10/1999 | Willeke | 209/132 |
| 5,997,619 | A | 12/1999 | Knuth et al. | 96/224 |
| 6,001,145 | A | 12/1999 | Hammes | 55/471 |
| RE36,489 | E | 1/2000 | Alexay | 250/343 |
| 6,024,923 | A | 2/2000 | Melendez et al. | 422/82.08 |
| 6,036,027 | A | 3/2000 | Grimes | 209/725 |
| 6,062,392 | A | 5/2000 | Birmingham et al. | 209/143 |
| 6,070,658 | A | 6/2000 | Cipriani | 165/166 |
| 6,082,439 | A | 7/2000 | Kato et al. | 165/79 |
| 6,082,445 | A | 7/2000 | Dugan | 165/167 |
| 6,101,886 | A | 8/2000 | Brenizer et al. | 73/863.23 |
| 6,110,247 | A | 8/2000 | Birmingham et al. | 55/442 |
| 6,125,845 | A | 10/2000 | Halvorsen et al. | 128/200.24 |
| 6,193,587 | B1 | 2/2001 | Lin et al. | 451/56 |
| 6,194,731 | B1 | 2/2001 | Jeys et al. | 250/461.2 |
| 6,217,636 | B1 | 4/2001 | McFarland | 95/216 |
| 6,235,002 | B1 | 5/2001 | Carver et al. | 604/183 |
| 6,240,768 | B1 | 6/2001 | Lemonnier | 73/28.05 |
| 6,267,016 | B1 | 7/2001 | Call et al. | 73/863.22 |
| 6,276,016 | B1 | 8/2001 | Springer | 14/71.1 |
| 6,284,025 | B1 | 9/2001 | Kreisberg et al. | 95/267 |
| 6,293,861 | B1 | 9/2001 | Berry | 454/255 |
| 6,324,927 | B1 | 12/2001 | Ornath et al. | 73/863.11 |
| 6,334,365 | B1 | 1/2002 | Linker et al. | 73/864.81 |
| 6,363,800 | B1 | 4/2002 | Call et al. | 73/863.22 |
| 6,370,406 | B1 | 4/2002 | Wach et al. | 600/310 |
| 6,386,015 | B1 | 5/2002 | Rader et al. | 73/31.05 |
| 6,392,313 | B1 | 5/2002 | Epstein et al. | 290/52 |
| 6,435,043 | B1 | 8/2002 | Ferguson et al. | 73/863.22 |
| 6,443,314 | B2 | 9/2002 | Shiraiwa et al. | 210/474 |
| 6,488,900 | B1 | 12/2002 | Call et al. | 422/173 |
| 6,511,854 | B1 | 1/2003 | Asanov et al. | 436/518 |
| 6,532,067 | B1 | 3/2003 | Chang et al. | 356/318 |
| 6,532,835 | B1 | 3/2003 | Saaski et al. | 73/863.21 |
| 6,567,008 | B1 * | 5/2003 | Sansone | 340/666 |
| 6,573,836 | B1 | 6/2003 | Gitis et al. | 340/603 |
| 6,610,977 | B2 | 8/2003 | Megerle | 250/287 |
| 6,613,571 | B2 * | 9/2003 | Cordery et al. | 436/48 |
| 6,639,733 | B2 | 10/2003 | Minano et al. | 359/728 |
| 6,684,682 | B2 * | 2/2004 | Stemmle et al. | 73/23.2 |
| 6,695,146 | B2 | 2/2004 | Call et al. | 209/143 |
| 6,707,539 | B2 | 3/2004 | Selinfreund et al. | 356/71 |
| 6,711,939 | B2 * | 3/2004 | Megerle et al. | 73/45.4 |
| 6,729,196 | B2 | 5/2004 | Moler et al. | 73/863.22 |
| 6,742,703 | B2 * | 6/2004 | Esakov et al. | 232/45 |
| 6,765,490 | B2 * | 7/2004 | Lopez et al. | 340/632 |
| 6,805,751 | B2 | 10/2004 | Allen | 134/1 |
| 6,826,422 | B1 | 11/2004 | Modell et al. | 600/407 |
| 6,829,919 | B2 | 12/2004 | Sioutas et al. | 73/865.5 |
| 6,834,533 | B2 | 12/2004 | Megerle | 73/45.4 |
| 6,852,539 | B2 * | 2/2005 | Cordery et al. | 436/1 |
| 6,867,044 | B2 * | 3/2005 | Cordery et al. | 436/1 |
| 6,885,440 | B2 | 4/2005 | Silcott et al. | 356/73 |
| 6,886,419 | B2 * | 5/2005 | Cordery et al. | 73/863.23 |
| 6,887,710 | B2 | 5/2005 | Call et al. | 436/53 |
| 6,888,085 | B2 * | 5/2005 | Spencer et al. | 209/584 |
| 6,908,567 | B2 | 6/2005 | Uziel | 216/66 |
| 6,949,147 | B2 | 9/2005 | Uziel et al. | 134/1 |
| 6,984,524 | B2 | 1/2006 | Nguyen et al. | 436/172 |

| | | | |
|---|---|---|---|
| 7,073,371 B2 * | 7/2006 | Strohmeyer et al. | 73/28.01 |
| 7,091,870 B2 | 8/2006 | Tsutsumi et al. | 340/632 |
| 7,096,125 B2 | 8/2006 | Padmanabhan et al. | 702/24 |
| 7,106,442 B2 | 9/2006 | Silcott et al. | 356/338 |
| 7,113,277 B2 | 9/2006 | Craig | 356/318 |
| 7,173,257 B1 | 2/2007 | Warrick et al. | 250/458.1 |
| 7,178,379 B1 * | 2/2007 | Strohmeyer et al. | 73/28.01 |
| 7,188,538 B2 * | 3/2007 | Beck | 73/865.8 |
| 7,205,152 B2 | 4/2007 | Swider | 426/1 |
| 7,261,008 B2 | 8/2007 | Saaski et al. | 73/863.22 |
| 7,265,669 B2 | 9/2007 | Call et al. | 340/539.26 |
| 7,304,259 B2 | 12/2007 | Schwarz et al. | 209/584 |
| 7,458,248 B2 * | 12/2008 | Carlson et al. | 73/31.07 |
| 7,503,204 B2 * | 3/2009 | Strohmeyer et al. | 73/28.01 |
| 7,543,478 B2 * | 6/2009 | Burroughs et al. | 73/28.01 |
| 7,578,973 B2 | 8/2009 | Call et al. | 422/83 |
| 7,591,980 B2 | 9/2009 | Call et al. | 422/91 |
| 7,720,567 B2 | 5/2010 | Doke et al. | 700/117 |
| 7,799,567 B1 | 9/2010 | Call | 436/53 |
| 2001/0047136 A1 | 11/2001 | Domanik et al. | 600/473 |
| 2003/0075593 A1 * | 4/2003 | Wood | 229/71 |
| 2003/0080550 A1 * | 5/2003 | Phillips | 283/116 |
| 2003/0085266 A1 * | 5/2003 | Simon | 232/27 |
| 2003/0115161 A1 * | 6/2003 | Cordery et al. | 705/402 |
| 2003/0115998 A1 * | 6/2003 | Belec et al. | 83/343 |
| 2003/0136203 A1 * | 7/2003 | Yoon | 73/864.33 |
| 2003/0144800 A1 * | 7/2003 | Davis et al. | 702/22 |
| 2003/0145664 A1 * | 8/2003 | Schwarz et al. | 73/863.22 |
| 2003/0193019 A1 * | 10/2003 | Nagano et al. | 250/281 |
| 2004/0028561 A1 | 2/2004 | Daugherty et al. | 422/99 |
| 2004/0063197 A1 | 4/2004 | Tilles et al. | 435/287.2 |
| 2004/0063198 A1 * | 4/2004 | Tilles et al. | 435/287.2 |
| 2004/0104342 A1 | 6/2004 | Yamada et al. | 250/288 |
| 2004/0124366 A1 | 7/2004 | Zeng et al. | 600/473 |
| 2004/0255644 A1 * | 12/2004 | Carlson et al. | 73/28.04 |
| 2005/0070025 A1 | 3/2005 | Mooradian et al. | 250/461.1 |
| 2005/0136540 A1 * | 6/2005 | Quine et al. | 436/1 |
| 2005/0181520 A1 * | 8/2005 | Ornath | 436/181 |
| 2006/0030790 A1 | 2/2006 | Braig et al. | 600/584 |
| 2006/0226998 A1 * | 10/2006 | Wilson | 340/632 |
| 2006/0257853 A1 | 11/2006 | Herman | 435/6 |
| 2008/0281528 A1 | 11/2008 | Relle, Jr. | 702/19 |

FOREIGN PATENT DOCUMENTS

| | | |
|---|---|---|
| KR | 10-0497514 | 7/2005 |
| KR | 10-0549222 | 2/2006 |
| WO | WO 98/58725 | 12/1998 |
| WO | WO 03/089661 A1 | 10/2003 |
| WO | WO 03/089907 | 10/2003 |
| WO | WO 2007/123349 | 11/2007 |

OTHER PUBLICATIONS de la Mora, J.F., "Aerodynamic Focusing of Particles and Heavy Molecules: Final Report." *NTIS*: 9pp., Jan. 8, 1990.

de la Mora et al., "Aerodynamic Focusing of Particles in a Carrier Gas." *Journal of Fluid Mechanics*. vol. 195: 1-21, Oct. 1988.

Fuerstenau et al., "Visualization of Aerodynamically Focused Subsonic Aerosol Jets." *Journal of Aerosol Science*. vol. 25, No. 1: 165-173, Jan. 1994.

Giechaskiel et al., "A metric for health effects studies of diesel exhaust particles," *Aerosol Science* vol. 40: 639-651, 2009.

Jensen et al., "Sampling and Characteristics of Bioaerosols." *NIOSH: Manual of Analytical Methods*: 82-112, Jan. 15, 1998.

Jurcik et al., "On the Shape of Impactor Efficiency Curves." *Journal of Aerosol Science*, vol. 26, No. 7: 1139-1147, 1995.

Kunzli et al., "Public health impact of outdoor and traffic-related air pollution: a European assessment," *Lancet* vol. 356: 795-801, 2000.

Lee et al., "Development and application of personal respirable particulate samplers (PRPS)," *Atmospheric Environment* vol. 40: 212-224, 2006.

Liu et al., "Optimizing the Detection Efficiency of a Low Pressure, In-Situ Particle Monitor Using Aerodynamic Focusing Lenses." 1996 Proceedings—Institute of Environmental Sciences: 217-224, 1996.

Noll et al., "Relationship between elemental carbon, total carbon, and diesel particulate matter in several undergound metal/non-metal mines," *Environmental Science & Technology* vol. 41, No. 3: 710-726, 2007.

Noll et al., "Using laser absorption techniques to monitor diesel particulate matter exposure," *Smart Biomedical and Physiological Sensor Technology, Proceedings of SPIE* vol. 6759: 11pp., 2007.

Primmerman, Charles., "Detection of Biological Agents." *Lincoln Laboratory Journal*, vol. 12, No. 1: 3-32, 2000.

Wittmaack, Klaus., "In search of the most relevant parameter for quantifying lung inflammatory response to nanoparticle exposure: particle number, surface area, or what?" *Environmental Health Perspectives* vol. 115, No. 2: 187-194, 2007.

Environmental Protection Agency (U.S.) "Health assessment document for diesel engine exhaust", EPA/600/8-90/057F: 669pp., May 2002.

Carrano, John. "*Ultraviolet Light.*" Spie's Oe magazine, Jun. 2003, pp. 20-23.

Cassarly, William. "*Taming Light.*" "*Non-imaging optical systems focus on transferring light efficiently and controlling its distribution.*" Oe magazine, Dec. 2002, 7pp.

Cousins, Daniel. "*Biodefense of Passenger Aircraft.*" Biodefense Systems Group, MIT Lincoln Labroratory. Presented at FAA Center of Excellence. 23pp., Jan. 19, 2005.

Foot, Virginia, E., et al. "*Characterising single airborne particles by fluorescence emission and spatial analysis of elastic scattered light.*" Defence Science and Technology Lab. (United Kingdom) 2pp, 2005 SPIE—The international Society for Optical Engineering.

Frye-Mason, Greg et al. "*Novel fluorescence-based integrated sensor for chemical and biological agent detection.*" Nomadics, Inc. (USA) 2pp, 2005 SPIE—The international Society for Optical Engineering.

Huston, Alan, L., et al. "*Optical classification of bioaerosols using UV fluorescence and IR absorption spectroscopy.*" Naval Research Lab. (USA) 2pp, 2005 SPIE—The international Society for Optical Engineering.

Jeys, T.H., L., et al. "*Development of UV LED based biosensor.*" SPIE vol. 5071, 2003 SPIE., pp. 234-240.

Kaye, Paul, H., et al. "*A low-cost multi-channel aerosol fluorescence sensor for networked deployment.*" University of Hertfordshire (UK) and Defence Science Technology Lab (UK) 11pp, 2005 SPIE—The international Society for Optical Engineering.

* cited by examiner

- EXPLOSIVES PARTICLES

- FILTER MEDIA: NICKEL FOAM FILTER
  - COLLECTION FLOW RATE: 100 LITERS PER MINUTE
    (NEED TO RECONSIDER UPPER CAPTURE LIMIT)
  - DESORPTION TEMPERATURE: 130°C
  - DESORPTION FLOW RATE: 30.5 ML/MIN
  - FLOW CONTROL: YES ON FIDO, NO ON MS
    (FLOW TO MS IS SET BY VACUUM SYSTEM)
  - TEMPERATURE CONTROL: YES ON FILTER HOLDER, YES ON TUBING DOWNSTREAM OF FILTER
  - DESORPTION FLOW SPLIT BETWEEN MS/MS AND FIDO: YES

FILTER — HOLDER — HEATING ELEMENT

*FIG. 4C*

- BIOLOGICAL AEROSOLS

- FILTER MEDIA: COMMERCIAL OFF THE SHELF HEPA FILTER
  - FLOW RATE: 100 LITERS PER MINUTE
  - SUPPLIER: MURTECH, INC.
  - FLOW CONTROL: NO

*FIG. 4D*

1. MS Vapor sample pump:
   - Q = 400 ml/min, adsorption mode
   - dP = 30" water 2. Fido Vapor sample suction pump:
   - Q = 400 mL/min, adsorption mode
   - dP = ??

- Fido Vapor Jet Pump:
  - Q = 80+LPM
  - dP = ??

1. Particulate Pre-concentrator Pump
   - Q = 400 l/min (?)
   - dP = XX" water

2. Air puffer compressor
   - Q = 10 lpm
   - dP = 30 psig

3. Air curtain blower
   - Q =1000 lpm
   - dP = 5" water

4. Vapor chamber drawdown pump
   - Q = 10 lpm
   - dP = 5" water

*FIG. 7A*

- MS rotary valve(s) – VICI Valco
  - Two position
  - Heated to 250 C (or less as required by explosives)
  - Stepper motor actuated

- Vapor chamber pressure drawdown valve
  - Solenoid actuated?
  - Normally closed, opened for 1 second per 30 second cycle

- Air puffer valve array
  - Pneumatically actuated?
  - Normally closed, each opened momentarily once per 30 second cycle

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| Vapor Sampling Module | | | | | | | | | | | | | | | | | | | | | | | | | | | | | | |
| Package conveyance On | | | | | | | | | | | | | | | | | | | | | | | | | | | | | | |
| Enclosure drop On | | | | | | | | | | | | | | | | | | | | | | | | | | | | | | |
| Vapor drawdown valve Open | | | | | | | | | | | | | | | | | | | | | | | | | | | | | | |
| Column adsorber pump On | | | | | | | | | | | | | | | | | | | | | | | | | | | | | | |
| Rotary valve to column sample | | | | | | | | | | | | | | | | | | | | | | | | | | | | | | |
| Column heater On | | | | | | | | | | | | | | | | | | | | | | | | | | | | | | |
| Rotary valve to direct sample | | | | | | | | | | | | | | | | | | | | | | | | | | | | | | |
| Column cooling fan On | | | | | | | | | | | | | | | | | | | | | | | | | | | | | | |
| Optional Peltier cooler On | | | | | | | | | | | | | | | | | | | | | | | | | | | | | | |
| Particle Sampling Module | | | | | | | | | | | | | | | | | | | | | | | | | | | | | | |
| Package conveyance | | | | | | | | | | | | | | | | | | | | | | | | | | | | | | |
| Puffer sequence On | | | | | | | | | | | | | | | | | | | | | | | | | | | | | | |
| Mesh sample pump On | | | | | | | | | | | | | | | | | | | | | | | | | | | | | | |
| Mesh heater On | | | | | | | | | | | | | | | | | | | | | | | | | | | | | | |
| Rotary valve to mesh sample | | | | | | | | | | | | | | | | | | | | | | | | | | | | | | |
| Always On | | | | | | | | | | | | | | | | | | | | | | | | | | | | | | |
| Vapor drawdown vacuum pump | | | | | | | | | | | | | | | | | | | | | | | | | | | | | | |
| DFU blower On | | | | | | | | | | | | | | | | | | | | | | | | | | | | | | |
| Puffer reservoir air pump | | | | | | | | | | | | | | | | | | | | | | | | | | | | | | |
| Air curtain blower | | | | | | | | | | | | | | | | | | | | | | | | | | | | | | |
| Aaburg s+B1 ampler blowers | | | | | | | | | | | | | | | | | | | | | | | | | | | | | | |

MS/MS timing: 1st ten seconds — analyze particles from previous package
2nd ten seconds — analyze direct sample of vapor from current package, while also adsorbing vapors
3rd ten seconds — desorb and analyze vapors from current package

MAIL PARCEL SCREENING USING MULTIPLE DETECTION TECHNOLOGIES

RELATED APPLICATIONS

This application is based on a prior copending provisional application, Ser. No. 60/916,972, filed on May 9, 2007, the benefit of the filing date of which is hereby claimed under 35 U.S.C. §119(e).

BACKGROUND

Ever since letters contaminated with weapons-grade *Bacillus anthracis* (anthrax) spores passed through the United States Postal Service (USPS) in the fall of 2001 and the "letter bombs" mailed in the 1980s, there has been a heightened awareness that chemical, biological, radiological or explosive threats could be hidden in an item of mail. Thus, there is an ongoing need to develop new technologies to address such potential threats. Due to the volume of mail that must be screened, it is desirable that any such screening technology be cost effective.

The USPS is not the only organization that delivers mail and parcels. Commercial shippers and the U.S. military also manage the shipment and delivery of large volumes of parcels. It would be desirable to provide a screening technology that is sensitive and cost effective. Such a technology will preferably be capable of screening for chemical, biological, radiological, nuclear or explosive (CBRNE) threats. Similarly, such a technology would be useful for screening luggage and cargo prior to transportation.

SUMMARY

Disclosed herein are a plurality of concepts for screening mail and parcels for a plurality of threats.

In one exemplary embodiment, a system is configured to automatically screen an item of mail for the presence of at least three different types of threat agents selected from a group consisting of a radiological agent, a toxic chemical agent, a bio-threat agent, and an explosive agent. In addition, the system also includes at least three of the following components: a radiation detection component, a toxic chemical detection component, a puffer-based bio-threat sampling component, and an explosive detection component. The radiation detection component is configured to detect if radiation is associated with the item of mail. The toxic chemical detection component is configured to determine if a toxic chemical agent is associated with the item of mail. The puffer-based bio-threat sampling component is configured to collect a bio-threat sample to be analyzed to determine if a bio-threat agent is present on the item of mail and it collects the bio-threat sample by filtering a gaseous fluid used to dislodge bio-threat particles associated with the item of mail. The explosive detection component comprises at least one element selected from a group consisting of: a vapor concentrator; a sampling medium configured to be directly swiped over a surface of the item of mail; and a puffer-based particulate sampler, the puffer-based particulate sampler being configured to collect particulates disposed on a surface of an item of mail. The explosive detection component is configured to determine if an explosive agent is associated with the item of mail. Even where a majority of the bio-threat agent, explosive agent, or toxic agent is contained within the parcel, it is highly likely that detectable traces will be present on the surface of the parcel. The system optionally includes an X-ray based imager. The system optionally includes the capability to measure the item's size and weight.

In another exemplary embodiment, a system is configured for automatically screening mail for CBRNE threats in an item of mail. The system comprises a radiation detection component, a relatively low flow sampling component, and a relatively high flow sampling component. The relatively low flow sampling component is configured to detect if either a toxic chemical agent or an explosive agent is associated with the item of mail, and it includes a mass spectrometer and an explosive detector. The relatively high flow sampling component is configured to automatically collect a bio-threat sample to be analyzed to determine if a bio-threat agent is associated with either the item of mail or a batch of mail containing the item of mail. The radiation detection component is configured to detect if radioactive material is associated with the item of mail. The system optionally includes a sizing component configured to determine at least one dimension of the item of mail. The system optionally includes a component to measure the weight of the item of mail.

In yet another exemplary embodiment, a mail screening system is configured to automatically screen an item of mail for at least one threat selected from the group consisting of CBRNE threats. The system includes a detector configured to analyze a sample collected by the system, where the sample is associated with the item of mail, to determine if at least one threat selected from the group consisting of CBRNE threats is associated with the item of mail. The system also includes an automated sample arm; a means to achieve a relative motion between the automated sample arm and the item of mail; a sampling substrate coupled to the automated sample arm, and means to intentionally remove the sample from the sampling substrate and convey the sample to the detector for analysis. In a particularly preferred but not limiting embodiment the detector is an explosives detector. The sampling substrate comprises a generally planar surface, and the automated sample arm is configured to position the sampling substrate such that the generally planar surface of the sampling substrate wipes a generally planar portion of the item of mail as the sampling substrate contacts the item of mail while there is relative motion between the automated sample arm and the item of mail. The system preferably includes a light curtain configured to determine at least one dimension of the item of mail, to facilitate proper positioning of the automated sample arm relative to the item of mail.

Another aspect of the concepts disclosed herein is an exemplary method for automatically screening an item of mail for at least one threat selected from the group consisting of CBRNE threats. A sampling substrate is positioned such that the sampling substrate is in contact with at least a portion of the item of mail. A relative motion is achieved between the sampling substrate and the item of mail, thereby collecting the sample on the sampling substrate, such that the sample is retained upon the sampling substrate until the sample is intentionally removed. When the sample is intentionally removed from the sampling substrate, it is conveyed to a detector configured to analyze the sample. The sample is analyzed with the detector to determine if at least one threat selected from the group consisting of CBRNE threats is associated with the item of mail. The sampling substrate is further regenerated for future use by heating the sampling substrate for a period of time sufficient to remove substantially all remaining traces of the sample from the sampling substrate. Preferably at least one dimension of the item of mail is determined before sampling, to facilitate properly positioning the sampling substrate relative to the item of mail.

In yet another exemplary method for automatically screening an item of mail for CBRNE threats, the item of mail is automatically scanned using a radiation detector that does not require obtaining a physical sample from the item of mail, in order to screen for radiological and nuclear threats. The item of mail is automatically screened for an explosive threat by collecting a sample from the item of mail by automatically wiping at least one surface of the item of mail using a sampling substrate that retains an explosive sample thereon until the explosive sample is intentionally removed. The sampling substrate is heated to volatilize at least a portion of the explosive sample, and the volatilized explosive sample is directed to an explosive detector. Further, a vapor based sample is automatically collected from an ambient gaseous environment proximate the item of mail and the vapor based sample analyzed to detect a chemical threat associated with the item of mail. A jet of gaseous fluid is automatically directed over at least a portion of the item of mail after collecting the vapor based sample, to dislodge any particles retained on the item of mail, and an ambient gaseous environment proximate the item of mail is filtered to remove particles entrained in the gaseous environment, thereby obtaining the particle based sample that can be tested for a biological threat.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 4C is a functional block diagram providing additional detail about the vapor sampling chamber of FIG. 4A, and conveying a vapor sample to an explosive detector for screening of explosive agents;

FIG. 4D is a functional block diagram providing additional detail about the particle sampling chamber of FIG. 4A, and collecting a bio-threat sample;

Figure 3A:
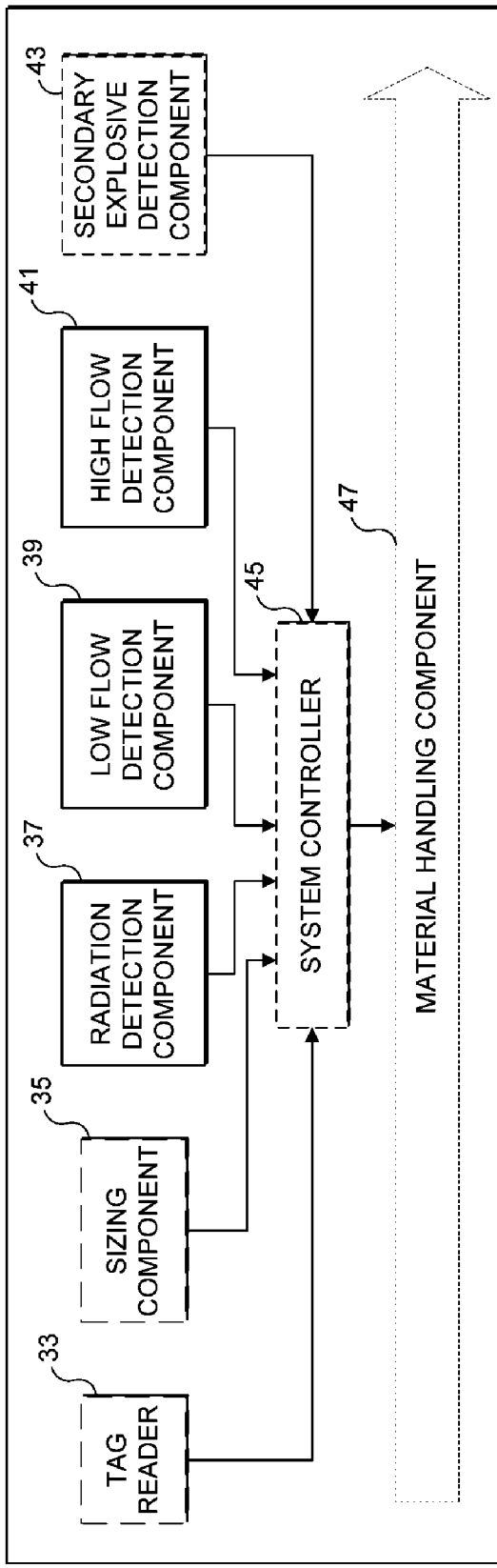
FIG. 3A is a high level block diagram illustrating the primary components of a second exemplary embodiment of a mail screening system, which automatically screens mail using both a low flow sampling component and a high flow sampling component.
Figure 8:
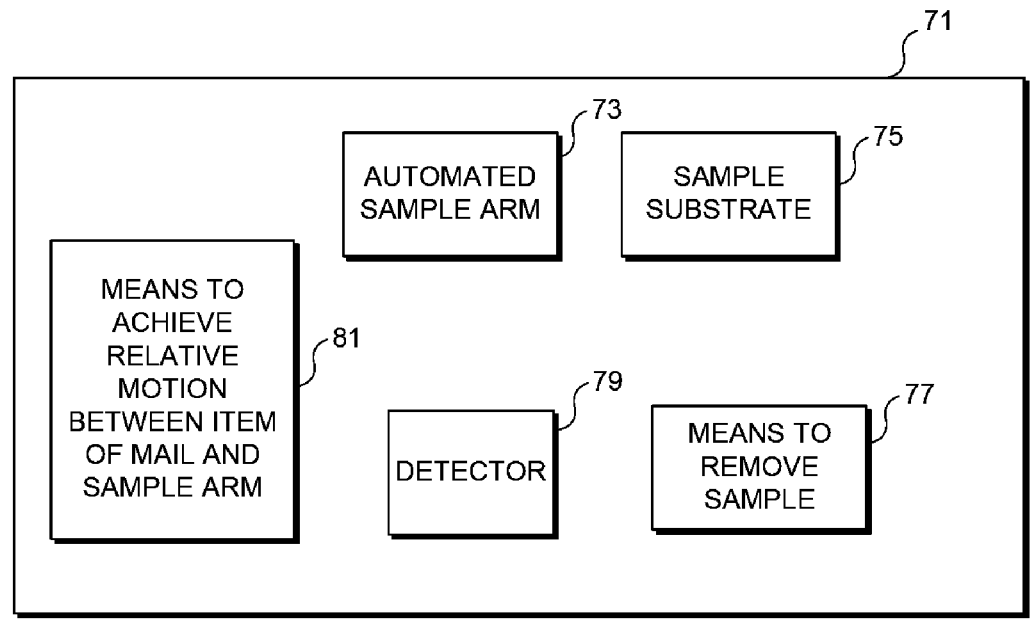
Figure 10:
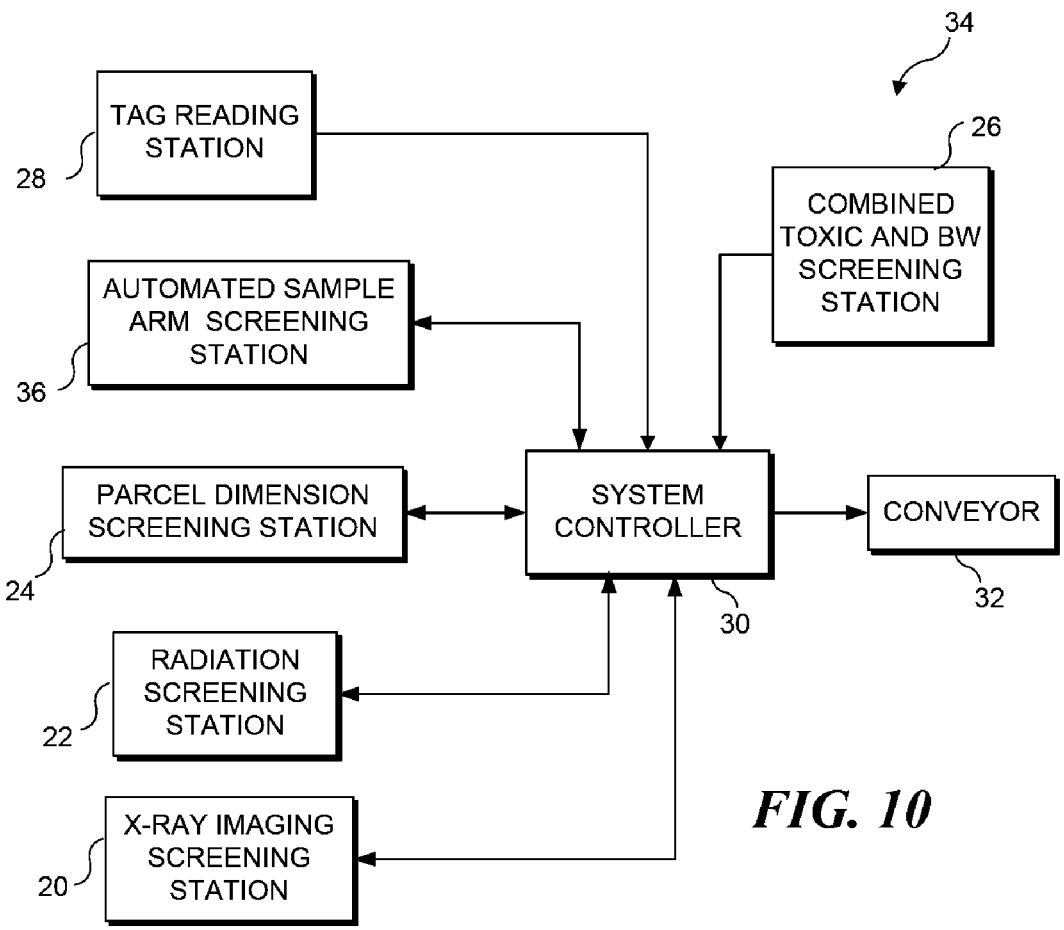
Figure 9:
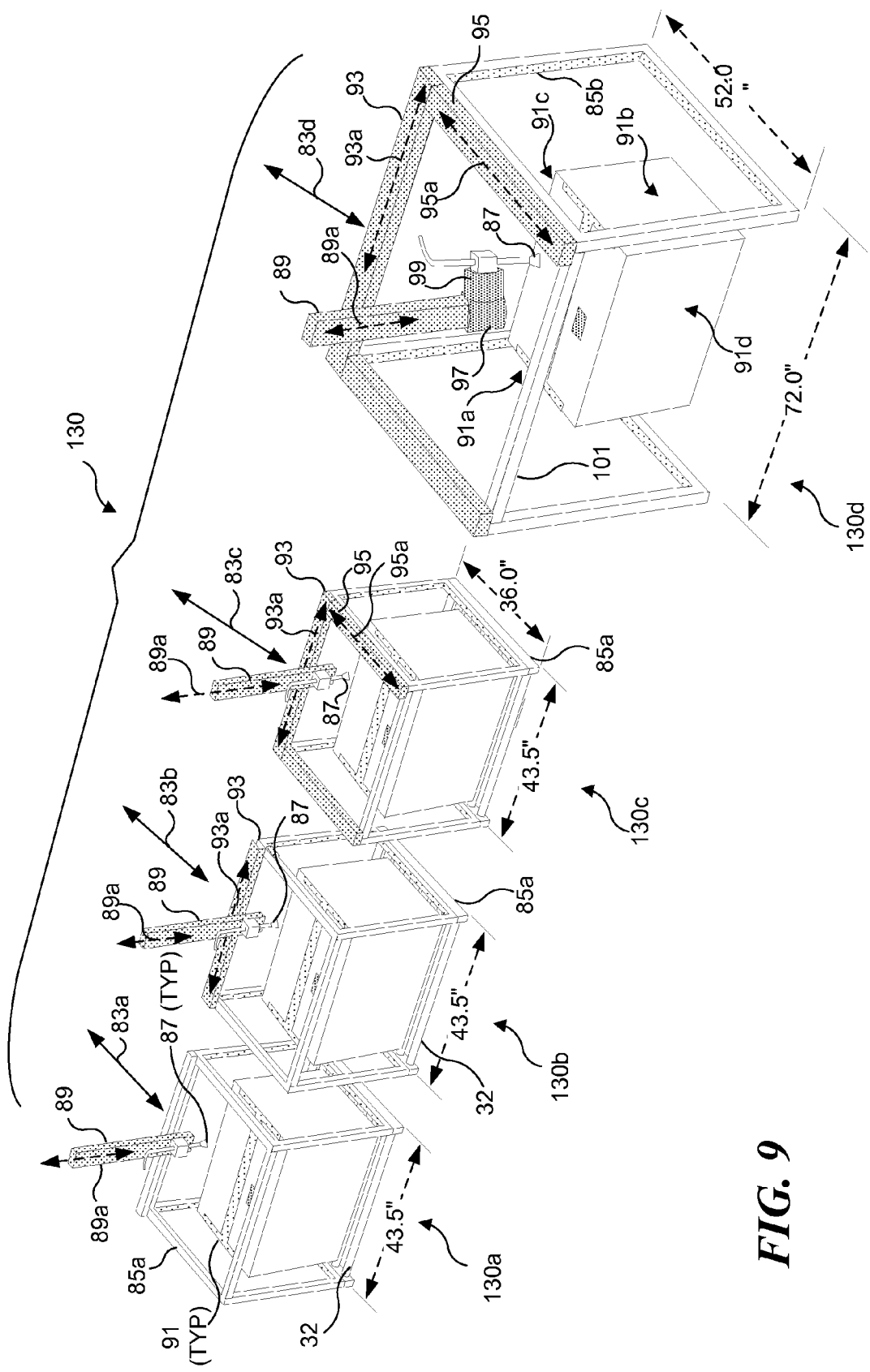
Figure 11:
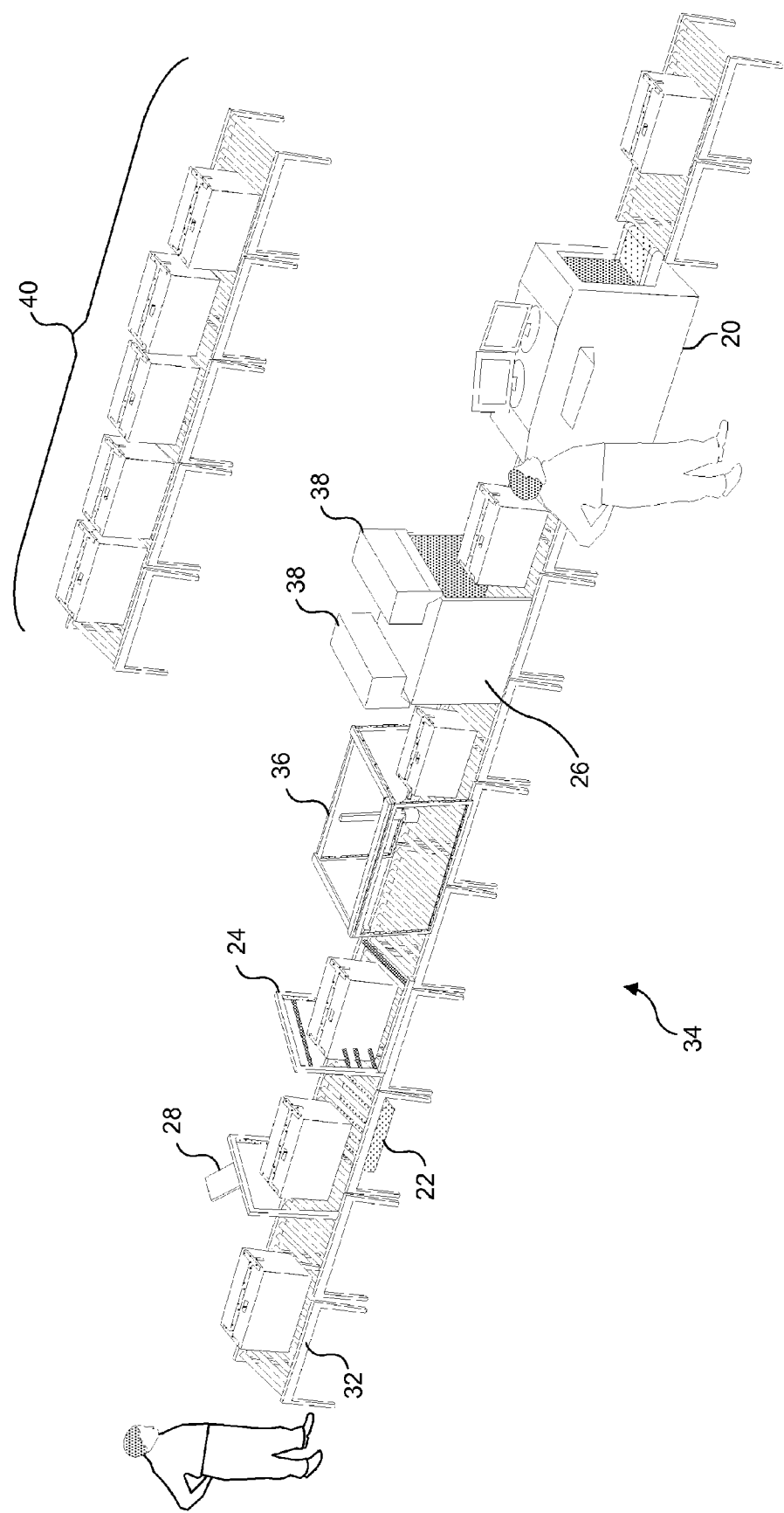
Figure 12:
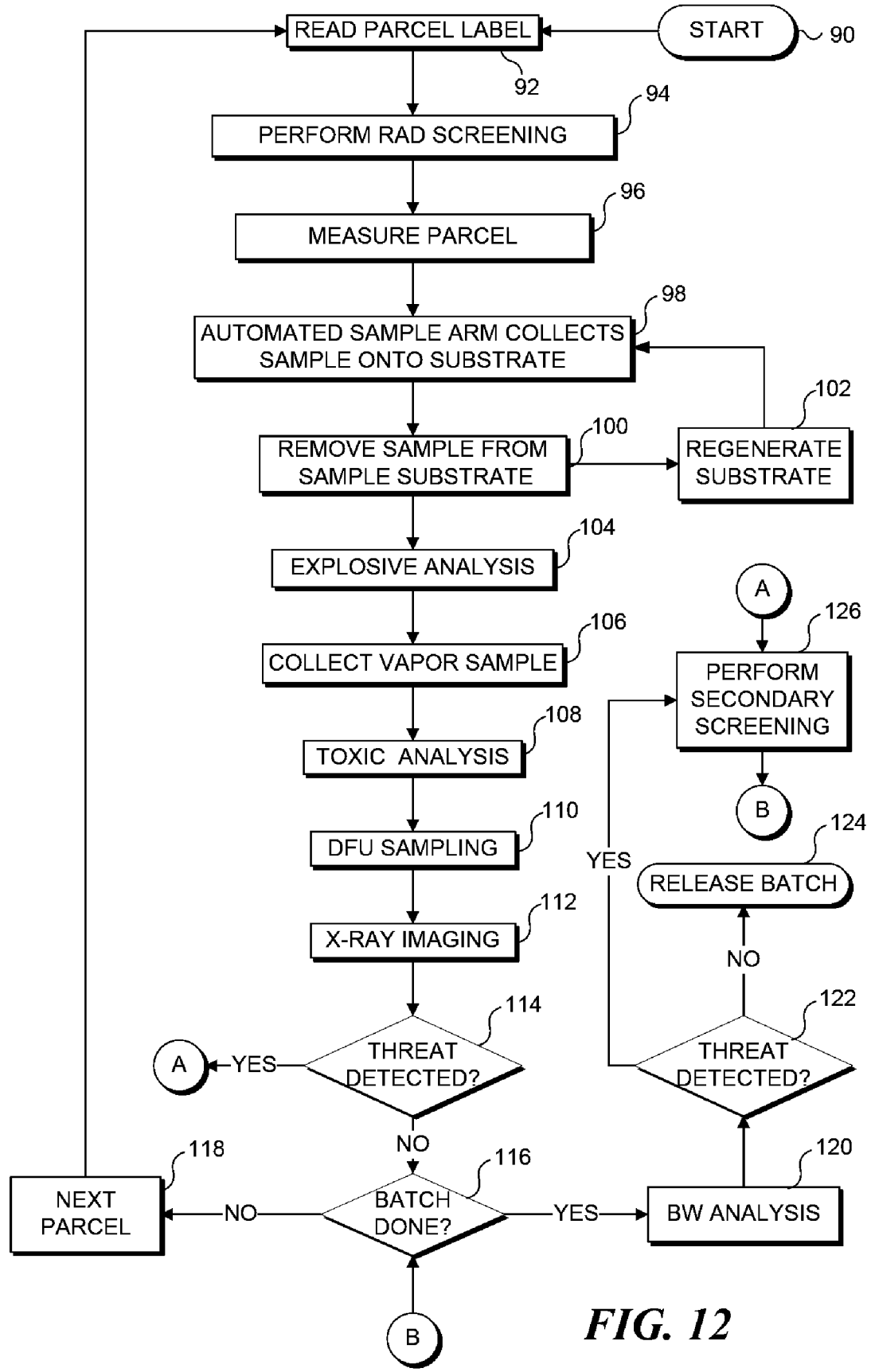

FIG. 7A summarizes exemplary pump specifications for use in various screening systems disclosed herein;

FIG. 7B summarizes exemplary valve specifications for use in various screening systems disclosed herein;

FIG. 7C summarizes exemplary control logic for screening systems disclosed herein that are based on the second exemplary embodiment of FIG. 3A;

FIG. 8 is a functional block diagram of an exemplary mail screening system that includes an automated sample arm;

FIG. 9 is an artist's representation of different embodiments of the automated sample arm of the mail screening system of FIG. 8;

FIG. 10 is a functional block diagram of yet another exemplary mail screening system that includes an automated sample arm;

FIG. 11 is an artist's representation of the mail screening system of FIG. 10; and FIG. 12 is a flow chart of steps for utilizing the mail screening system of FIG. 10.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

The exemplary embodiments described herein facilitate CBRNE threat screening of a variety of types of mail. Significantly, such screening systems can be readily integrated into the existing military mail sorting process. It should be recognized that the concepts disclosed herein are not limited to screening mail for the military; rather, the concepts disclosed herein can be beneficially employed to screen parcels for the military and other users. As used herein, the phrase item of mail is intended to encompass parcels, packages and letters, and any container, box, or case in which an item is packed for shipping and delivery. The term parcel, as used herein, is thus also intended to include luggage and any container packed with personal belongings for transportation on airplanes, cruise ships, or trains.

Various portions of the specification and claims refer to sampling for a hazardous material on the surface of a parcel, or a hazardous material associated with a parcel. The term surface of a parcel encompasses all external surfaces of a parcel (noting that a statement or claim reciting that a surface of the parcel is sampled simply indicates that at least one external surface is sampled, not necessarily all external surfaces). The term associated with should be understood to include hazardous materials that are contained within a parcel, in addition to hazardous materials disposed on an external surface of a parcel. Hazardous materials on the surfaces of parcels are generally deposited on the outer surface of a parcel by individuals responsible for placing the hazardous material in the parcel (it is surprisingly difficult to avoid leaving traces of such hazardous materials on external parcel surfaces). Hazardous materials on surfaces of a parcel can be sampled either by dislodging the hazardous material (using for example, jets or puffs of compressed gases such as air, vibrating the parcel, or using high intensity flash lamps to vaporize hazardous material from parcel surfaces), or by physically wiping a portion of the external parcel surfaces using a sampling substrate (followed by removing the sample from the substrate for analysis). Hazardous materials contained within a parcel are generally more difficult to sample. However, parcels can be scanned to detect any radiation that might be emitted from a radioactive material contained within a parcel. Air samples from the exterior surface of a parcel can be collected to obtain a sample of a volatile material leaking out of a parcel in trace amounts. X-ray images can be used to determine if the parcel includes any sealed containers that might merit closer examination of that parcel. Less desirably, very small openings (i.e., openings too small to negatively affect the structural integrity of a parcel) can be made in a parcel to collect a sample of air contained within the parcel.

Before discussing specific screening system embodiments in detail, it may be helpful to first explain the types of components that can be used to detect the chemical, explosive, biological and radiation threats, and then describe exemplary screening system embodiments which employ one or more of such components.

Material Handling Equipment: While not specifically required, material handling equipment, such as conveyor systems (generally a conveyor belt similar to those employed in conventional mail processing rooms and baggage handling systems in airports, or roller conveyors employed in warehouse facilities), can be beneficially incorporated into the screening systems disclosed herein.

Design Considerations: Exemplary, but not limiting, design considerations include the following. Providing modular and scalable screening systems. Providing mail/parcel screening systems capable of achieving a parcel throughput of about 30 seconds or less. Providing mail/parcel screening systems that require no more than two operators per system. Providing mail/parcel screening systems capable of screening parcels up to 2'×3'×4' in dimension. Providing mail/parcel screening systems including the ability to track individual parcels using radio frequency identification (RFID) tags, such that RFID tag readers can be incorporated into any of the systems described below. Providing screening systems configured to screen mail for one or more of the following types of threat agents: chemical agents, explosive agents, biological agents and radiological/nuclear agents.

Parcel Identification and System Control: In an exemplary, but not limiting embodiment, each parcel or item of mail is individually labeled with a unique identifier, such that data collected by the screening system unique to that parcel or item of mail can be stored in a database. RFID tags and machine readable optical codes (such as barcodes) represent exemplary identification technologies. A computer (i.e., a processor combined with a memory storing software to be executed by the processor) represents a particularly preferred type of system control. Such a computer can control system components such as material handling equipment, valves, fans, pumps and blowers (which may be employed in various sampling and detection components), detectors (which may include one or more of explosive detectors, toxic chemical detectors, radiation detectors, and bio-threat samplers and/or bio-threat detectors), and operator interfaces. The computer will collect and store data from each of the sensors, and evaluate the data to trigger an alarm (audible, visual, or a combination thereof) when a threat is detected. It should be recognized that other types of controllers, such as custom circuits and hardwired controllers, could also be employed.

Vapor Sampling for Detecting Traces of Explosives/Chemicals: A critical factor in reliable detection of explosives or other trace residues on parcels is effective sampling. Research and development efforts have often focused on increasing a sensor's sensitivity to target analytes. Regardless of how sensitive a detector is, it will only successfully detect explosives if a sufficient sample is properly collected and delivered to the sensor. Collection of explosive analyte is complicated by the fact that the equilibrium vapor pressure of many explosives is very low. Further, the flux rate of explosive vapor from contaminated surfaces is low, and this flux is typically into a large volume of air. Once explosive vapor is liberated from a surface, it diffuses through the boundary layer of air near the contaminated surface and mixes with the air outside the boundary layer. Turbulent dispersion mechanisms lead to dispersion of the vapor away from its source. The plume of vapor that results can be highly fragmented, resulting in a heterogeneous sampling space that contains air that is mostly free of explosive.

Trace detection attempts over very large sample volumes have an extremely low probability of detection, even if there are volumes of air that contain sufficient concentrations of analyte. Unless the contaminated surface has stayed in a region of stagnant air, the concentration of explosive vapor in the air near an explosive device is very low, likely orders of magnitude below that of the equilibrium vapor concentration. To overcome this problem, pre-concentrators are utilized to enrich the concentration of target analyte in a sample. Pre-concentrators contain a substrate coated with or constructed from a material that sorbs (sometimes selectively) target analyte vapors from air as the air is drawn through the pre-concentrator. Once the desired volume of air is run through or over the pre-concentration medium, the pre-concentrator is typically heated rapidly to desorb the target analyte from the sorbent material, and the vapor generated is then entrained into a low volume flow of carrier gas that sweeps the sample into a sensor for analysis. In this way, the explosive vapor from a relatively large volume of air is delivered to the sensor in a relatively smaller volume of air, effectively increasing the concentration of explosive in the sample.

To maximize the probability of collecting enough vapor on the pre-concentration medium, many systems either collect vapor for long periods of time at relatively low to relatively medium flow rates, or collect for shorter time periods with relatively higher flow rates. Both of these techniques have significant problems with respect to mail screening. First, there are finite limits to the maximum flow rates, as a function of the pre-concentration surface. In general, the lower the flow rate across the surface, the higher the percentage of particles that are deposited upon the surface. As the flow rate increases, the probability of the target vapor particles being deposited upon the pre-concentration medium actually begins to decrease. This problem can be diminished by increasing the size of the pre-concentration surface, while lowering the flow rate (keeping the volumetric flow constant). However, too much of an increase will then necessitate a second stage of pre-concentration before the sample is in a small enough volume to present to currently available trace detectors in a timely fashion. In short, bulk sampling of the vapor head space over the surface of a target is an impractical solution for field deployment, due to the extended time periods required for both low sampling rates and higher sampling rates combined with a secondary desorption.

Alternatively, particles containing or comprised of explosive material can be stripped from the surface of the parcel with the use of pulsed air jets (puffers) or with an "air knife," and then filtered or concentrated. Since this approach liberates the aerosol into a relatively large volume of air, two techniques have been employed to concentrate the explosive. In portals currently used to screen passengers in airport security check points, puffers are coupled to high-flow-rate filters. After the filtering is completed, the filter is heated to thermally desorb the explosive vapor. Alternatively, a virtual impactor can be used to concentrate the particulates prior to deposition onto a thermal desorption surface.

As an alternative to puffer-based or bulk air sampling, directional sampling provides great benefits in reducing the volume of air sampled in order to collect the same number of useful particles for deposition onto the pre-concentration medium. An Aaberg nozzle is an exemplary structure that can be used for directional vapor sampling. The straightforward benefits of directional suction versus simple suction devices are based in the fact that simple suction devices draw fluid from all directions equally, and consequently as the distance of the target volume of air from the input nozzle grows, the volume of air that must be sampled in order to achieve capture of target particles increases at a cubic rate. The relationship between the distance from the target and the increased volume of air required for sampling becomes a squared relationship. Additionally, the Aaberg nozzle increases the speed of the moving air, decreasing sample time.

As will be described in greater detail below, in at least one embodiment disclosed herein, a mail/parcel screening system will include a relatively large (½" diameter) Vorberg nozzle. The nozzle is set at a pre-determined height above the target parcel, and the nozzle runs in Aaberg mode for four (4) to five (5) seconds, sucking up any vapor particles onto a pre-concentration medium. After the Aaberg mode sampling completes, the nozzle will switch into vortex mode, and will then collect particulate material from the surface of the parcel. The two phases of sampling will collect onto separate media so that following the vapor collection phase, the desorption process can be performed on the vapor collection medium while the particle collection phase is proceeding. By pipelining the vapor and particulate testing in this fashion, the overall throughput rate of the system can be increased. In other words, a single nozzle will initially collect vapors, and will then be operated in a vortex mode to collect particles. Such a screening system is configured to collect and provide sample material to both explosive and chemical detection system components during screening.

With respect to chemical screening, in at least some of the screening systems disclosed herein, a sampling subsystem will interconnect with and supply concentrated material to an integrated mass spectrometer for evaluation of potential chemical threats. Preferably, the instrument will be capable of two levels of mass spectrometry, or MS/MS. The capability of using two levels of mass spectrometry yields additional levels of molecular fingerprinting, wherein signals of interest are isolated from the background clutter and further processed to generate highly reproducible, low-noise secondary signatures for chemical identification and confirmation. This tandem MS detection process provides the necessary sensitivity and specificity to distinguish a wide range of targeted chemical compounds in complex matrices in a very rapid analysis.

With respect to explosive screening, in at least some of the screening systems disclosed herein, a sampling subsystem will provide material for trace explosives detection.

In addition to puffers and air knives, other techniques for dislodging traces of hazardous materials from a parcel include applying a physical force to a parcel (such as vibrating a parcel, or slapping the parcel with a member designed to apply a force to the parcel without damaging the parcel), or heating the parcel (for example, by passing the parcel through a heated chamber), or directing flashes of high intensity light at parcel surfaces to remove hazardous materials that may be disposed on the surface of the parcel (heat may also induce materials disposed within the parcel to be volatile and leak out such that they can be detected). With respect to the use of flash lamps, the delivery of energy to the parcel surfaces during a very short period of time (flash lamps characteristically are energized very briefly) likely heats the air immediately adjacent to the parcel surface, which provides turbulence to remove particles from the surface of the parcel. This phenomenon is likely at least as important with respect to removing particles as any heating of the parcel surface that might occur.

Radiation Threat Detection Components: In at least one exemplary embodiment, the screening system is capable of automatically screening all items of mail in order to determine whether or not the item of mail is a source of radiation. In one configuration, the device utilized to determine whether or not a source of radiation is present in an item of mail is a radiation scintillation portal. The radiation scintillation portal is utilized as a broad, non-specific screening step. If a signal is detected indicative of a radiological material, the detection is followed up with a secondary screening that is manual. This secondary screening is directed to providing a more specific radiological identification step in order to determine if the initial signal is a benign detection or a signal indicative of a dirty bomb or even Special Nuclear Materials. An advantage of this automated detect and manual identify technique is cost; the scintillation portals that simply detect radiation are significantly less expensive than technologies that automatically detect and identify a radioisotope.

A more expensive alternative is to employ a detector that can automatically detect the presence of radiation and to identify the source of the radiation. One such device is based on a NaI(Tl) gamma ray detector with digital electronics that can detect radioactivity at levels equivalent to 5 nano Curies of unshielded Cs-137. Naturally occurring isotopes, especially K-40, will be identified and give no alarm. The detector assembly is stabilized and calibrated. A two (2) inch lead and steel enclosure ensures shielding of background radiation and provides for high detection efficiency. The measurement time per parcel can be adjusted and defines the minimum detectable activity (MDA)—e.g., 7 seconds: 10 nCi; 30 seconds: 5 nCi; 60 seconds: 3.5 nCi; 120 seconds: 2.5 nCi. However, it is assumed that the system measurement time will normally be determined by explosives sampling and detection requirements. Those skilled in the art will recognize that actual MDAs may vary from the nominal values provided above. Note that the incorporation of the detect and identify technology provides more than the broad, non-specific screening step provided by the radiation scintillation portal. More specifically, the radiation level of the actual parcel as well as the detected threat isotope is displayed on a central computer. Thus, the use of this system component negates any manual secondary screening for identifying the isotope. In addition, in case of an alarm, in some embodiments such technology can be configured to display a warning message, activate a warning indicator light, send a warning message to another member of the security team, or activate an audible alarm.

Biological Threat Detection Components The explosive detection components, toxic chemical detection components, and radiation detection components discussed above detect such threats in real-time (i.e., for each item of mail individually, while that item of mail is moving through the screening system). In order to achieve a functional screening system of modest cost, many of the screening systems disclosed herein will incorporate an automatic bio-threat sampling subsystem, which is configured to collect an aggregate sample for a batch of mail processed in the screening system. For example, a single bio-threat sample can be accumulated over a four or eight hour shift or for a particular batch of mail. Prior to releasing that batch of screened mail for delivery, the aggregate bio-threat sample is analyzed. If no bio-threat is detected, then the batch of mail is released for delivery. If a potential bio-threat is found, the batch is set aside for further investigation, to identify the item or items of mail comprising the source of the bio-threat agent. Real-time sensors for bio-threats would be preferable to batch testing for bio-threats, but the sensors that are commercially available today suitable for this purpose rely upon laser-induced fluorescence detection, and such techniques are known to have high false alarm rates in the presence of paper dust. If a suitable sensor for real-time detection of bio-threats in the presence of paper dust were to become available in the future, it would be desirable to incorporate such a sensor into the biological sampling component.

In an exemplary embodiment, but not limiting embodiment, air proximate each item of mail in a batch of mail is filtered to collect a bio-threat sample. In at least one embodiment, jets of gaseous fluid are directed at each item of mail, so that any particles on the surface of the item of mail become entrained in the gaseous fluid, to be filtered by a dry filter unit (DFU). Apparatus configured to provide such fluid jets are commonly referred to as puffers or air knives (as they puff air/fluid at an object). It should be noted that the vapor sampling discussed above could be considered to correspond to a low flow environment, whereas collecting the bio-threat sample using a puffer would be considered to be a high flow environment.

In at least one embodiment, the item of mail is placed into a chamber that is isolated from the ambient environment (using either a physical barrier, a pressure barrier, or an air curtain). Air from within the chamber is continuously passed through the DFU to obtain the bio-threat sample. Air from puffers or air knives may also be added to the chamber to provide some high-shear, turbulent airflow at the surface of the parcel to help aerosolize any biological threats which may be present.

Screening system operators can determine how to break up large volumes of mail into batches, such that a bio-threat sample is collected from the DFU for each batch. Smaller batch sizes have the advantage of containing fewer items of mail that need to be individually examined if a bio-threat sample indicates that one of the items of mail in the batch contains a bio-threat. Larger batch sizes have the advantage of enabling larger volumes of mail to be processed without interrupting the screening operations to remove a bio-threat sample from the DFU. Custom DFUs can be fabricated to enable a filter change without interrupting the screening process (i.e., by enabling rapid filter change).

In at least one exemplary embodiment, a separate aerosol collector is employed to collect an additional bio-threat sample (i.e., in addition to the bio-threat sample collected by the DFU). If desired, the separate aerosol collector can be connected to an automated biological agent identification system. In yet another alternative configuration, a real-time biological-threat sensor can also be incorporated. In such a configuration, the real-time biological-threat sensor can be used to activate the agent identification system to analyze the sample for specific biological agents. Automated biological agent identification systems are commercially available, and are based on either polymerase chain reaction (PCR) amplification and detection of gene sequences associated with specific bio-threats (if present), or on antibody-antigen binding.

X-Ray Imaging Based Explosive Screening In some embodiments disclosed herein, an X-ray imaging based explosive screening component is incorporated into the screening system (preferably in addition to the other explosive detection technologies discussed above). In one exemplary embodiment, the X-ray screening component automatically images each item of mail, and a trained operator reviews the image to look for signs of an explosive agent. Useful X-ray imaging systems include 2-D X-ray, backscatter X-ray, two-power X-ray, and computed tomographic (CT) scanning (or 3-D) X-ray.

In the alternative, no operator reviews the X-ray images as they are acquired, rather an expert system configured to automatically analyze each image collected is employed. Thus, in the event that the software analyzing the scanned image detects a potential threat, the X-ray system can send a signal to the system controller indicating that a secondary screening is necessary, such as a review of the image by a trained operator.

In yet another embodiment, no operator reviews the X-ray images as they are acquired; rather the image generated by the X-ray component is stored in a database. Thus, in the event that a threat is detected, the stored image can be retrieved and analyzed in a secondary screening.

In an exemplary embodiment, the X-ray system is disposed at a predetermined distance from the radiation threat detector system components. This distance is a function of the distance required to prevent X-rays generated by the X-ray imaging subsystem from interfering with the radiation detection component. Shielding can be incorporated to reduce the deleterious impact of stray X-rays.

Figure 1:
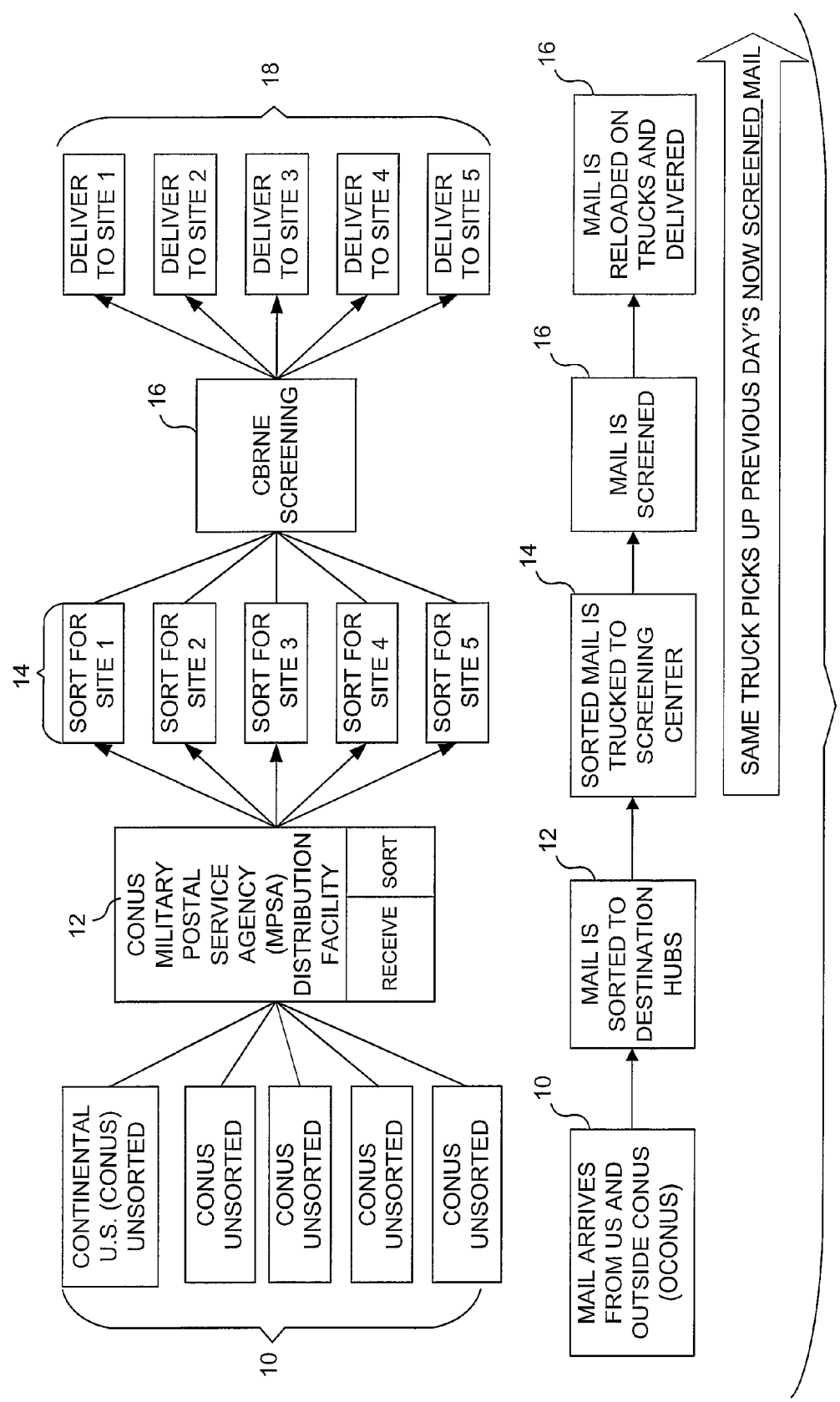
FIG. 1 is a block diagram illustrating a typical United States military mail sorting process modified to include one or more of the novel mail screening techniques disclosed herein.

FIG. 1 illustrates an exemplary embodiment of a mail screening process in which the CBRNE screening concepts disclosed herein are incorporated into the existing military mail sorting process. Mail arrives at a distribution center 10 from all over the Continental United States (CONUS) and Outside Continental United States (OCONUS). The mail is received at one or more Distribution Facilities 12, where the mail is sorted according to a plurality of destination sites 14 (for example, the sorted mail can be loaded into a dedicated truck or container according to the designated destination site), according to existing Military Postal Service Agency (MPSA) operations. The sorted mail is then received at a CBRNE screening center 16, where mail is screened in batches according to destination sites (note the use of screening center 16 is a modification to existing MSPA operations, and such a modification can be performed without adversely effecting normal operations). In this exemplary embodiment, it is assumed that a truck (or equivalent transport mechanism) that drops off a current batch of sorted but unscreened mail will collect a subsequently delivered sorted batch of mail that has been screened, the previously sorted and screened mail now being considered safe for delivery at a plurality of sites 18. In this exemplary embodiment, it is expected that a twenty-four (24) hour turn-around time to complete the screening process is readily achievable.

Figure 2A:
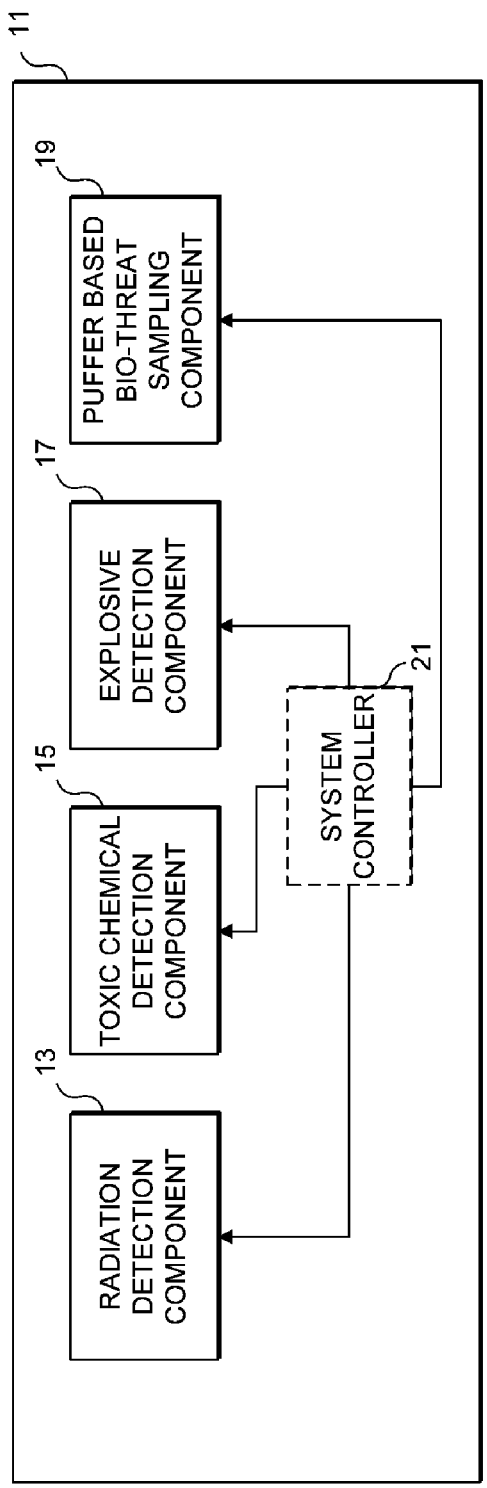
FIG. 2A is a high level block diagram illustrating the primary components of a first exemplary embodiment of a mail screening system, which automatically screens mail using at least three different screening technologies.

FIG. 2A is a high level block diagram illustrating the primary components of a first exemplary embodiment, a system 11 that is configured to automatically screen an item of mail for the presence of at least three different types of threat agents selected from a group consisting of a radiological agent, a toxic chemical agent, a bio-threat agent, and an explosive agent. System 11 thus includes at least three of the following: a radiation detection component 13, a toxic chemical detection component 15, an explosive detection component 17, and a puffer-based bio-threat sampling component 19. Radiation detection component 13 is configured to detect if radiation is associated with the item of mail. Preferably system 11 includes a controller 21 (such as a computer or less desirably a hard wired control circuit) logically coupled to each detection component.

An exemplary radiation detection component is a scintillation portal, such as are available from Saint-Gobain, Atlantic Nuclear, Thermo-Fisher, and ICx Technologies. Preferably the radiation detector will be capable of detecting and identifying even small amounts of shielded radioactive material, although it should be recognized that a simpler embodiment would provide automatic detection without identification. Such embodiments are somewhat less preferred, as they would require secondary screening of the parcel to identify the isotope that triggered the alarm. In a particularly preferred embodiment, the radiation detector will be sensitive to levels equivalent to five nano-curies of unshielded cesium-137, and naturally occurring isotopes, especially potassium 40, will be identified and will not trigger an alarm. Similarly, medical or industrial isotopes can be identified as such. In at least one embodiment, the radiation level of the item of the mail, as well as the detected threat isotope, will be displayed on an operator user interface (or controller 21). When a radioactive threat is detected and identified, a warning message can be displayed on the operator user interface, and if desired a color-coded light can be activated to indicate the threat level. Audible or electronic message alarms can be activated if desired.

Toxic chemical detection component 15 is configured to determine if a toxic chemical agent is associated with the item of mail. In a particularly preferred embodiment, the toxic chemical detection component includes a gas chromatograph mass spectrophotometer (GC/MS). A particularly preferred analytical instrument is available from ICx Technologies, Inc. (Arlington, Va.), which provides a rugged direct sampling mass spectrometer capable of multiple levels of mass spectrometry, or MS/MS. This capability provides additional levels of molecular fingerprinting, as signals of interest are isolated from the background clutter and further processed to generate highly reproducible, low noise secondary signatures for chemical identification and confirmation. This secondary process provides the necessary sensitivity and specificity to distinguish a wide range of targeted chemical compounds in complex matrices in a very rapid analysis. In one exemplary but not limiting implementation, the toxic chemical detection component includes a sampling chamber into which an item of mail is placed, while the GC/MS (or MS/MS) continuously samples the ambient air in the sampling chamber, in order to screen for toxic chemical agents. Those of ordinary skill in the art will readily recognize that in order to succeed in detecting trace levels of low-volatility chemical contaminants, particular attention must be paid to designing the sample interface between the source (i.e., the item of mail) and the sensor. Various types of sample interfaces can be beneficially employed, including heated transfer lines between the two points.

The explosive detection component is configured to determine if an explosive agent is associated with the item of mail. As indicated in FIG. 2B, explosive detection component 17 comprises at least one element selected from a group consisting of: a vapor concentrator 17a; a sampling medium 17b configured to be directly swiped over a surface of the item of mail; and a puffer-based particulate sampler 17c (the puffer-based particulate sampler being configured to blast particles off of an item of mail using a compressed fluid such as air, and then to collect such particulates). Details of a preferred automated system for swiping a sample off of an item of mail are provided below. In an exemplary, but not limiting embodiment, the explosives detector incorporated into explosive detection component 17 utilizes an amplifying fluorescence polymer (AFP) to detect trace levels of explosive materials in parts per quadrillion (ppq) quantities. Such a system is marketed under the name Fido®, and is available from ICx Technologies, Inc. (Arlington, Va.). AFP based explosive sensors can detect low femto-gram masses of TNT. This level of sensitivity far exceeds the capabilities of any other available detection system, including laboratory instruments. This technology sensitivity to plastic explosives is equivalent to or better than ion mobility spectrometer (IMS) technology (although it should be recognized that in some embodiments IMS can be used in place of AFP). Vapor phase sampling does not require physical contact with a contaminated surface. Articles contaminated with particles of explosives will produce explosive vapors as molecules of the explosive sublime from particles or desorb from surfaces. In at least one embodiment, both a vapor explosive sample and a particle explosive sample are automatically collected and analyzed for the presence of an explosive agent. In yet another embodiment, two different AFP based detectors are employed, where each detector is operating at a different temperature. This allows optimal sensitivity to different explosive compounds. Once again, a properly designed sample interface is required, and the explosives detection component can employ sample interfaces generally similar to those described above with respect to the toxic chemical detection component. Indeed, in at least one embodiment, the toxic chemical detection component and the explosive detection component share a common sample interface.

It should be noted that some explosives may be detectable using the toxic chemical detection component. For example, explosives that themselves are relatively volatile, or which include a detection taggant (i.e., a volatile chemical intentionally added to an explosive to render the explosive more readily detectable) can generally be detected using the same type of detector employed for the toxic chemical detection component (i.e., a GC/MS). Even when some explosives can be detected using the toxic chemical detection component, it is still desirable to include a separate explosive detection component (such as an AFP detector or an IMS detector), to detect less volatile explosive agents that are not as readily detectable using the toxic chemical detection component.

Puffer-based bio-threat sampling component 19 is configured to collect a bio-threat sample to be analyzed to determine if a bio-threat agent is present in the item of mail and it collects the bio-threat sample by filtering a gaseous fluid used to dislodge bio-threat particles associated with the item of mail. Note that the sample is collected automatically (such that the functions of radiation detection component 13, toxic chemical detection component 15, explosive detection component 17, and puffer-based bio-threat sampling component 19 are automated), but the analyzing step need not be automated. In at least one embodiment, a dry filter unit (DFU) is used to collect the bio-threat sample from a batch of mail (i.e., from a plurality of items of mail). Once the total batch is processed, a sample is obtained from the filter, and an analysis (such as a polymerase chain reaction (PCR) based analysis) is performed on the sample. A positive analysis will indicate that one or more items of mail in the batch are potentially contaminated with a bio-threat agent. Due to the difficulties of obtaining real time detection of bio-threats, this batch based analysis enables a system including a relatively high throughput (i.e., screening of an additional item of mail once every thirty seconds or less) to be achieved at a relatively modest cost. In a preferred but not limiting embodiment, the entire screening time for a single item of mail may be more than thirty seconds, particularly where the screening system includes a plurality of screening stations, but an item of mail will preferably pass through each screening station in about thirty seconds or less. More preferably, an item of mail will pass through each screening station in less than 10 seconds.

Figure 2C:
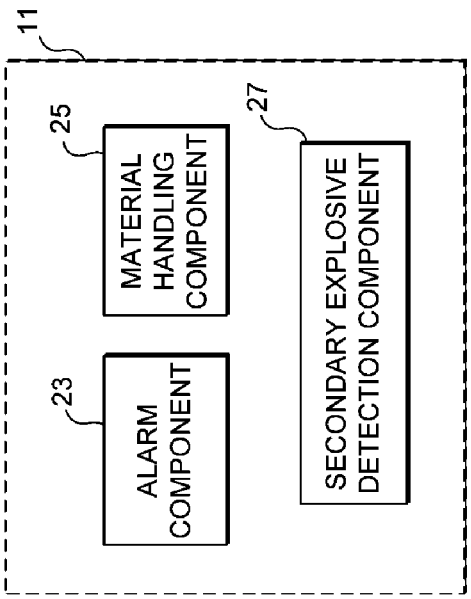
FIG. 2C is a block diagram illustrating different optional components that can be incorporated into the first exemplary embodiment of FIG. 2A.
Figure 2B:
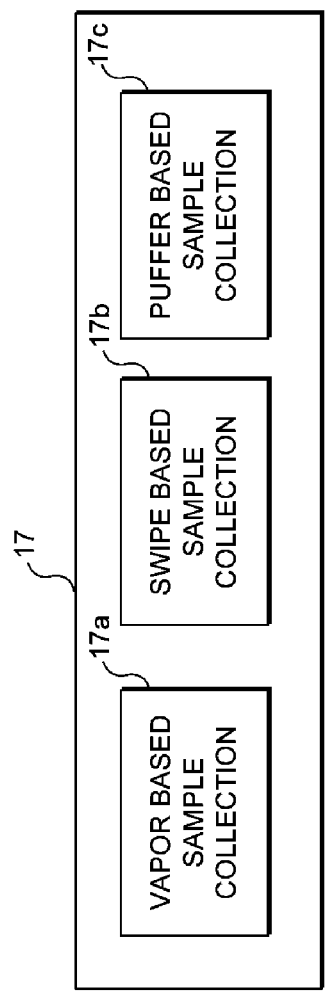
FIG. 2B is a block diagram illustrating three different types of components that can be employed in the explosive detection component portion of the first exemplary embodiment of FIG. 2A.

As indicated in FIG. 2C, system 11 can include one or more additional elements, such as an alarm component 23, a material handling component 25 (to facilitate movement of the items of mail through the screening system), and a secondary explosive detection component 27. The alarm component can include one or more audible or visual alarms configured to alert personnel to the detection of a potential threat. The alarm component can include a hard wired or wireless communication capability, to provide an indication of the presence of a threat condition to a remote location. In at least one exemplary embodiment the material handling component is a conveyor belt based system as indicated above. In at least one exemplary embodiment the secondary explosive detection component is an X-ray based imager. Generally, explosive detection via X-ray imaging requires the use of a trained operator to visually review images from each item of mail. Many different types of X-ray imaging can be employed, including 2D and 3D imaging.

Figure 3C:
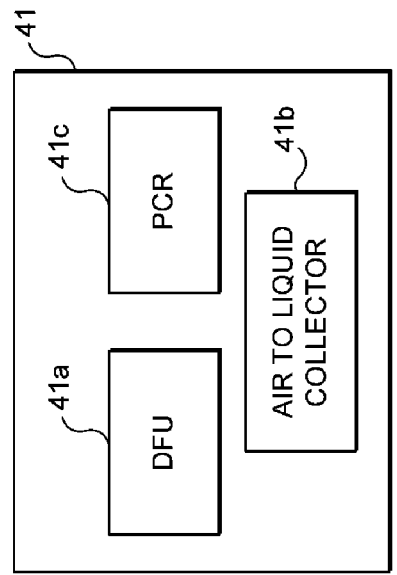
FIG. 3C is a block diagram illustrating details relating to the high flow sampling component portion of the second exemplary embodiment of FIG. 3A.
Figure 3B:
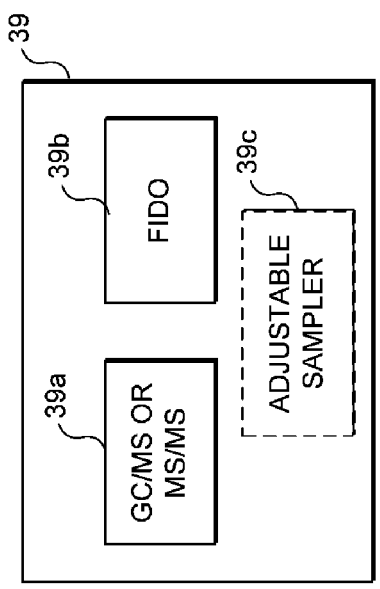
FIG. 3B is a block diagram illustrating details relating to the low flow sampling component portion of the second exemplary embodiment of FIG. 3A.
Figure 3D:
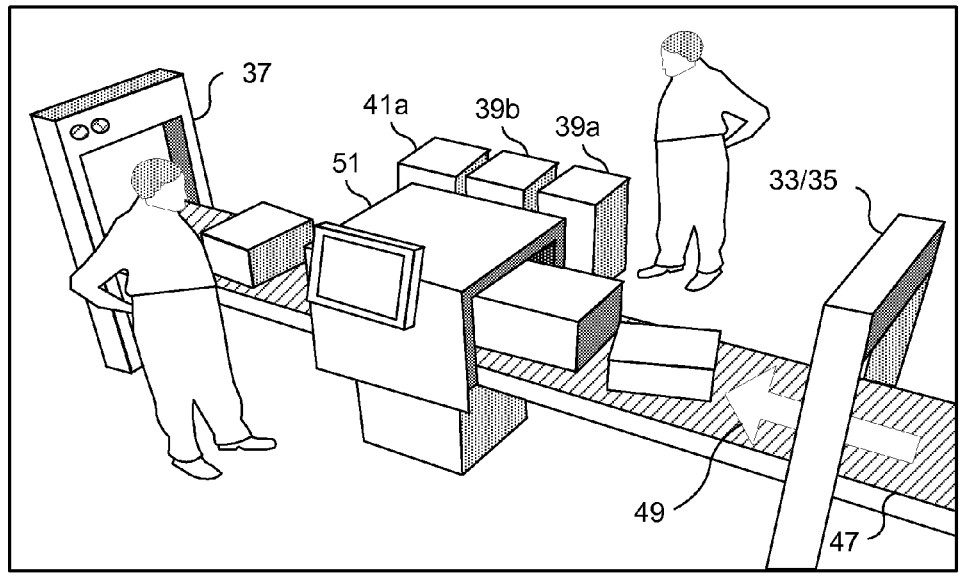
FIG. 3D is an artist's representation of the second exemplary embodiment of FIG. 3A.

In another exemplary embodiment, schematically illustrated in FIG. 3A, a system 31 is configured for automatically screening mail for CBRNE threats in an item of mail. FIG. 3D is an artist's representation of system 31. Referring once again to FIG. 3A, the system comprises a radiation detection component 37 (functionally equivalent to that described in association with FIG. 2A), a relatively low flow sampling component 39, and a relatively high flow sampling component 41. The radiation detection component is configured to detect if radioactive material is associated with the item of mail. The relatively low flow sampling component is configured to detect if either a toxic chemical agent or an explosive agent is associated with the item of mail, and includes a mass spectrometer 39a and an explosive detector 39b (as indicated in FIG. 3B). The relatively high flow sampling component is configured to automatically collect a bio-threat sample to be analyzed to determine if a bio-threat agent is associated with either the item of mail or a batch of mail containing the item of mail, and preferably includes a DFU 41a, an air-to-liquid collector 41b (such as the collector marketed under the trade name BioXC™ 200 by ICx Technologies, Inc. Arlington, Va.) and a bio-threat analyzer 41c (such as the automated PCR-based analyzer marketed under the trade name GeneXpert® by Cepheid, Inc., Sunnyvale, Calif.), as indicated in FIG. 3C. The system optionally includes one or more of a material handling component 47, a system controller 45, and a secondary explosive detection component 43, generally as described above. Significantly, the X-ray imaging element (secondary explosive detection component 43) is physically spaced apart from the radiation detection component, so that interference from the X-ray imager in the detection of radioactivity is minimized. Additional optional components include a tag reader 33 (configured to associate a unique ID placed on each item of mail with data collected by the system for that item of mail) and a sizing component 35 (configured to determine at least one dimension of the item of mail). Exemplary, but not limiting tag technologies include optical bar codes and RFID. An exemplary, but not limiting implementation of sizing component 35 is a light curtain. Preferably the height and width of the item of mail (often a parcel) is measured by the sizing component.

In embodiments employing relatively high flow sampling environments, the use of a virtual impactor to concentrate the sample prior to collection on a filter or in a direct-to-liquid sampler may be desirable.

Data from sizing component 35 can be used to enhance the performance of the low flow detection component. As noted above, particularly when the item of interest is present in low quantities, the sample interface is important. Adjustable sampler 39c preferably uses data from sizing component 35 to ensure that the adjustable sampler is properly positioned relative to the item of mail. For example, in at least one exemplary embodiment, the adjustable sampler is a nozzle configured to collect vapors emanating from the item of mail. Based on the dimensions determined by sizing component 35, the nozzle can then be moved closer to the item of mail, to collect a better vapor sample. The collected vapor sample can then be directed to one or more of mass spectrometer 39a and explosives detector 39b. In yet another exemplary embodiment, the adjustable sampler is a sampling substrate configured to collect a particle sample from a surface of the item of mail. Based on the dimensions determined by sizing component 35, the sampling substrate can then be placed in contact with the item of mail, to collect a particle sample. The collected particle sample can then be conveyed to one or more of mass spectrometer 39a and explosives detector 39b. Preferably, the sampling substrate is heated such that at least a portion of the collected particles vaporize, and the vapors are collected and directed to one or more of mass spectrometer 39a and explosives detector 39b. Where the system is collecting a vapor sample for analysis with GC/MS or MS/MS, it is preferable to physically move the nozzle close to the parcel, to maximize the concentration of the analyte in the sample. However, the system could be configured to just sample the air from a chamber the parcel is enclosed within. In embodiments in which the nozzle is physically moved, and the system is using Fido™ (or a similar detector) to detect explosive vapors, a single nozzle could be employed. Of course, two separate nozzles could be employed, and the engineering required for the two nozzle embodiment is likely to be less complicated.

In yet another exemplary embodiment, one or both of the low flow detection component and the high flow detection component includes a housing that defines a sampling volume. While such housings are not strictly required, they can reduce a level of vapors and particles not associated with an item of mail that are introduced into the sample. FIG. 3D is an artist's representation of an exemplary (but not limiting) implementation of system 31 that includes a single housing, and FIG. 3E is a block diagram of a variant that includes a separate housing for the low flow sampling component and the high flow sampling component.

Referring to FIG. 3D, an arrow 49 indicates the direction of parcels moving through the system. A parcel is labeled with an RFID tag and loaded onto the conveyor (i.e., material handling component 47). The parcel passes through an initial portal that combines tag reader 33 and sizing component 35, and the parcel height and width is measured. The parcel passes into a housing 51. Once inside the housing, the conveyor stops (by tripping an optical switch) and a position of adjustable sampler 39c (see FIG. 3B) is properly positioned based on the measured parcel dimensions. A vapor and/or particle sample is collected and conveyed to mass spectrometer 39a and explosive detector 39b. While the parcel is temporarily motionless, an operator views an X-ray image of the parcel (i.e., secondary explosive detection component 43). Once the operator has acquired and reviewed the X-ray image, the conveyor is reenergized. As the parcel exits housing 51 it passes through high flow detection component 41a, which preferably employs a puffer based dry filter collection unit, generally as described above. The parcel then moves through radiation detection component 37, completing the screening process. It should be recognized that FIG. 3D simply represents one possible embodiment, and does not necessarily represent an optimal embodiment. For example, the radiation detection component and the X-ray imager may not be spaced sufficiently far enough apart to prevent the X-rays from interfering with the radiation detector. Furthermore, using a single housing to implement the low flow detection component and the high flow detection component may be problematic unless the housing is sufficiently large enough to prevent the high flow being used to collect the bio-threat sample from interfering with the low flow vapor sampling. It may be desirable to implement the low flow detection component and the high flow detection component spaced farther apart, or in separate housings. Significantly, the low flow detection component must come before the high flow detection component, such that the high flow rates associated with the high flow detection component do not disperse the vapors or particles to be collected in the low flow detection component.

Figure 3E:
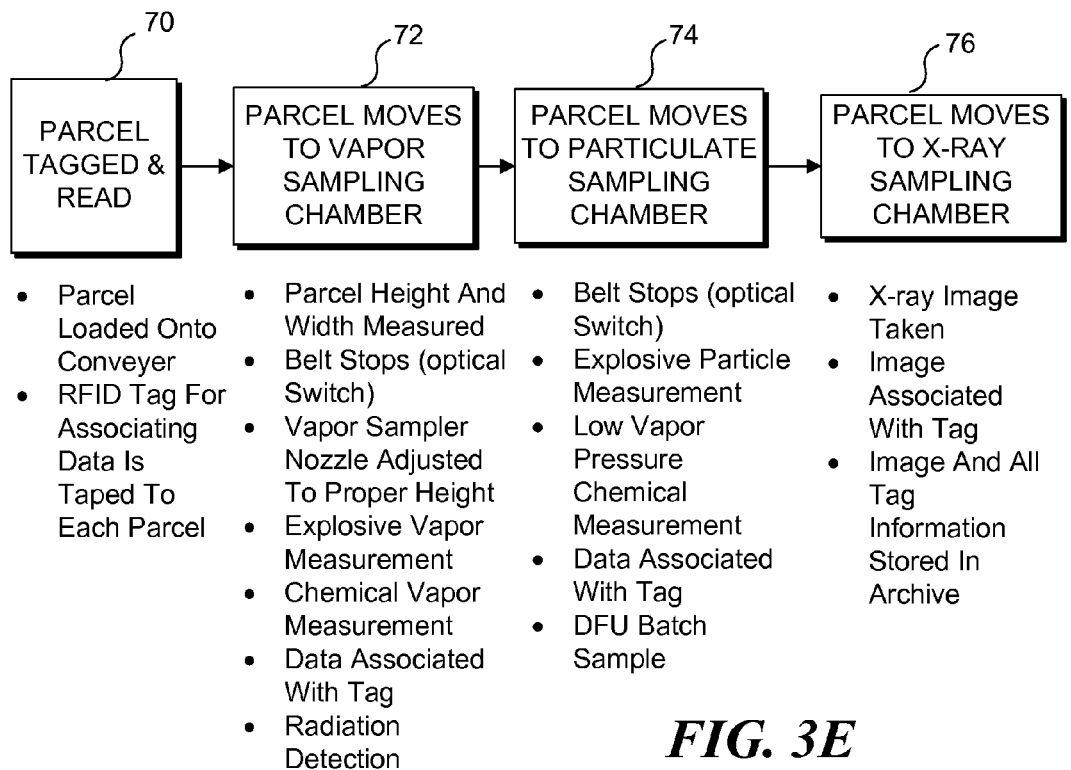
FIG. 3E is a functional block diagram based on the second exemplary embodiment of a mail screening system, providing additional detail about the functions of major components.

FIG. 3E is a functional block diagram illustrating a modification of system 31 (FIG. 3A), in which separate housings are employed for the low flow sampling component and the high flow (or particle) sampling component. More specifically, in a block 70, a first parcel is tagged with an RFID tag (and the RFID tag is read), so it can be uniquely identified and loaded onto the conveyor belt. In one exemplary embodiment, the conveyor belt is configured to be controlled via an optical switch. After a thirty (30) second interval, the conveyor belt automatically advances the first parcel into a vapor sampling chamber (i.e., the low flow detection component), as shown in block 72, where, for example, the parcel dimensions are measured. Of course, it should be recognized that the sizing operation could be performed at the time the RFID tag was read, or at some point in between the start of the conveyor and the vapor sampling chamber. Note that a second parcel (which was previously tagged, measured, and sampled in the vapor sampling chamber) is simultaneously advanced to the particulate sampling chamber, as indicated in a block 74, while a third parcel (previously in the particulate sampling chamber) is advanced to an X-ray screening station as indicated in a block 76 (understanding that the secondary explosive screening performed by the X-ray screening is not implemented in all embodiments). The process is repeated once each thirty (30) seconds, and thus, the system processes one hundred and twenty (120) parcels per hour.

Returning to a discussion of the handling of the first parcel, in the vapor sampling chamber indicated in block 72, exemplary screening operations include the detection of explosives, explosive taggants and chemical warfare agents (i.e., the detection of both explosive agents and toxic chemical agents) by obtaining a vapor sample and conveying the vapor sample to the appropriate detectors (i.e., a GC/MS or MS/MS for toxic chemical agents, and an explosive detector, such as an AFP based detector (i.e., FIDO®)). If desired, radiation screening can be performed in the vapor sampling chamber (using a suitable radiation detector, such as the radiation detectors discussed above). In at least one exemplary but not limiting embodiment, an adjustable sample nozzle is positioned close (i.e., within several millimeters) to the parcel based on previously determined parcel dimensions, to collect a quality vapor sample. Since each parcel has a unique RFTD tag, the test data from each sensor (i.e., radiation detector, toxic chemical detectors, and explosive detector) is stored in a database, which associates the data collected for each parcel with that parcel's RFID tag.

After samples have been acquired in the vapor sampling chamber, the parcel is then advanced to the particulate sampling chamber as indicated in block 74, where the presence of the parcel is detected (via an optical switch in an exemplary but not limiting implementation), and the conveyor belt is stopped once again. In this particulate sampling chamber, exemplary screening operations include the detection of explosives, explosive taggants and chemical warfare agents (i.e., the detection of both explosive agents and toxic chemical agents) by obtaining particle samples and conveying the particle sample to the appropriate detectors (i.e., a GC/MS or MS/MS for toxic chemical agents, and an explosive detector, such as an AFP based detector (i.e., Fido®)). In an exemplary, but not limiting embodiment, a sampling substrate is positioned (based on a previously determined parcel size) so as to contact the parcel and to collect a particle sample. The collected particle sample can then be conveyed via a robotic positioning element with a gripper holding the sampling substrate to one or more of mass spectrometer 39a and explosives detector 39b (see FIG. 3B). Preferably, the sampling substrate is heated such that at least a portion of the collected particles vaporize, and the vapors are collected and directed to one or more of mass spectrometer 39a and explosives detector 39b. In addition, the DFU continuously collects particulates from the particulate sampling chamber and deposits them onto a filter media to produce a bio-threat sample. As noted above, while the bio-threat sample is automatically collected, the analysis of the sample is performed as a manual operation (at least with respect to moving the bio-threat sample to a detector). Preferably, a sample is retrieved from the DFU after a batch of mail is processed, to enable a relatively large number of parcels to be screened relatively quickly. Thus, with respect to the bio-threat sample, a secondary screening operation provides for analysis of the bio-threat sample. In an alternative and preferred embodiment, a bio-threat sample is automatically collected with an air-to-liquid collector, and the liquid sample can be automatically pumped or gravity fed directly into the automated bio-threat analyzer, such that no manual handling of the bio-threat sample is required. The DFU may optionally be operated in parallel to provide a sample archive suitable for laboratory verification of the results from the automated analyzer. As noted above, test data from each sensor associated with the particle sampling chamber is stored in a database which associates the data to each parcel. It should be recognized that in some embodiment, the particle sampling chamber collects only a bio-threat sample. In embodiments where a toxic chemical sample or an explosive sample is collected in the particle sampling chamber, it may be feasible to use a common toxic chemical detector (GCMS or MS/MS) or explosive detector for both the vapor sample (collected in the previous chamber) and the particle sample. The use of a common detector will require a sample conveyance structure (such as fluid lines) to direct the sample to the detector. The use of a common detector will likely require synchronization between the analysis of the vapor samples and particle samples, and the use of a detector that performs relatively rapid analyses, to avoid introducing undesirable delays in the screening process.

The parcel is then advanced to the X-ray sampling chamber (block 76), where for example, an image is taken of the parcel and an operator visually reviews the image for the presence of an explosive agent. Since each parcel has a unique RFTD tag, the image from the sensor is stored in a database which associates the image to each parcel.

With respect to screening for radioactivity, as noted above a preferred detector will be capable of indicating both the presence of radioactivity, and the specific isotope emitting the radiation. If a simpler detector is employed (i.e., a detector capable only of identifying the presence of radioactivity, but not the source of the radiation), a secondary screening operation can be manually performed on the parcel to identify the radioisotope source, utilizing hand held radiation identification devices, or taking a sample for analysis using non-portable detectors, so that a definitive identification of the source of the radiation can be made. The parcel is then advanced to the particulate sampling chamber as shown in block 76 via an optical switch, for example, that stops and starts the conveyor belt.

Figure 4A:
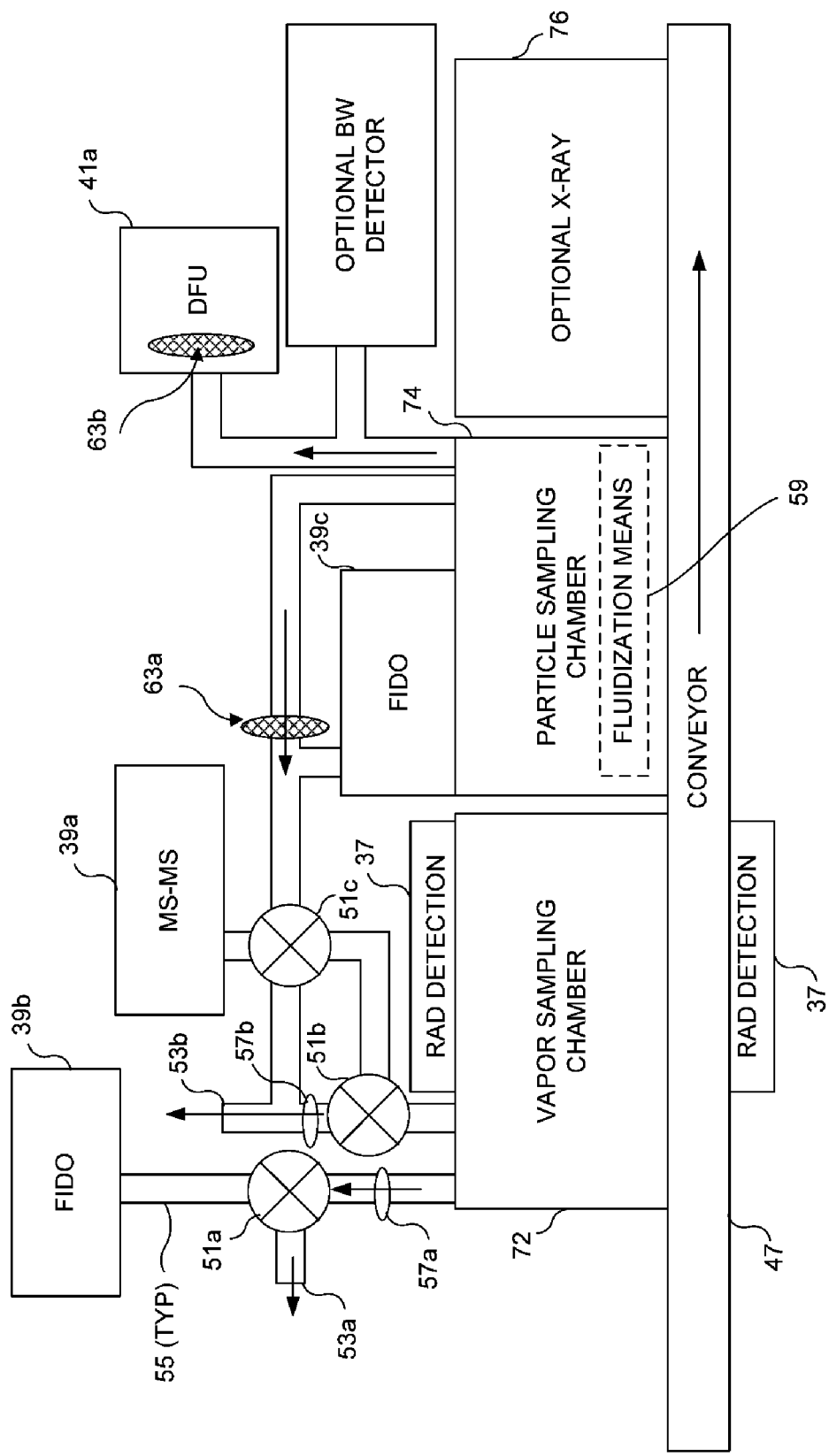
FIG. 4A is a functional block diagram based on the second exemplary embodiment of a mail screening system, providing additional detail about the structure of major components.

FIG. 4A is a functional block diagram illustrating yet another modification of system 31 (FIG. 3A), enabling an exemplary (but not limiting) configuration of fluid valves 51a, 51b, and 51c and fluid lines 55 coupling the sampling chambers to the various detectors to be visualized. The chambers are similar to conventional X-ray chambers used in airports. The functional purpose of the chambers is to enclose moving parts and to minimize disturbance to nearby persons from the system, and to minimize contamination (such as perfumes) being deposited onto the items of mail caused by nearby persons. In this particular embodiment, valve 51a selectively places vapor sampling chamber 72 (i.e., the sampling chamber associated with low flow detection component 39, understanding that the detection component includes the sampling chamber as well as the associated detectors, valves, fluid lines, etc.) in fluid communication with an outlet 53a or explosives detector 39b via a first set of fluid lines 55. A vapor pre-concentrator 57a is disposed between valve 51a and the vapor sampling chamber. Valve 51b allows sampling from vapor pre-concentrator 57b (into mass spectrometer 39a) or directly from vapor sampling chamber 72 (into mass spectrometer 39a) through valve 51c. Note valve 51c also allows the desorbed analyte from pre-concentrator 57b or from filter 63a to be directed to mass spectrometer 39a for analysis. Note that in this embodiment, radiation detection component 37 extends above and below the vapor sampling chamber. Referring now to the particulate sampling chamber 74 (i.e., the sampling chamber associated with high flow detection component 41, understanding that the detection component includes the sampling chamber as well as the associated detectors, valves, fluid lines; etc.), fluid lines 55 convey particulates entrained in a fluid (such as air) to DFU 41a (which includes a removable filter 63b for capturing a bio-warfare (BW) sample (i.e., the bio-threat sample), an optional BW detector, and to an additional explosives detector 39c (note the presence of a filter 63a disposed between the particle sampling chamber and the additional explosive detector; details on this filter will be provided below in connection with the description of FIG. 4C). Note that the particulate sample chamber includes fluidization means 59 (such as a puffer), which directs pressurized fluid towards the item of mail, to remove particles associated with the item of mail. Furthermore, it should be noted this variation includes the secondary explosive detection component (the X-ray imager). Not specifically shown in this embodiment, but which are preferably employed, are the previously described system controller and parcel tag reader.

Figure 4B:
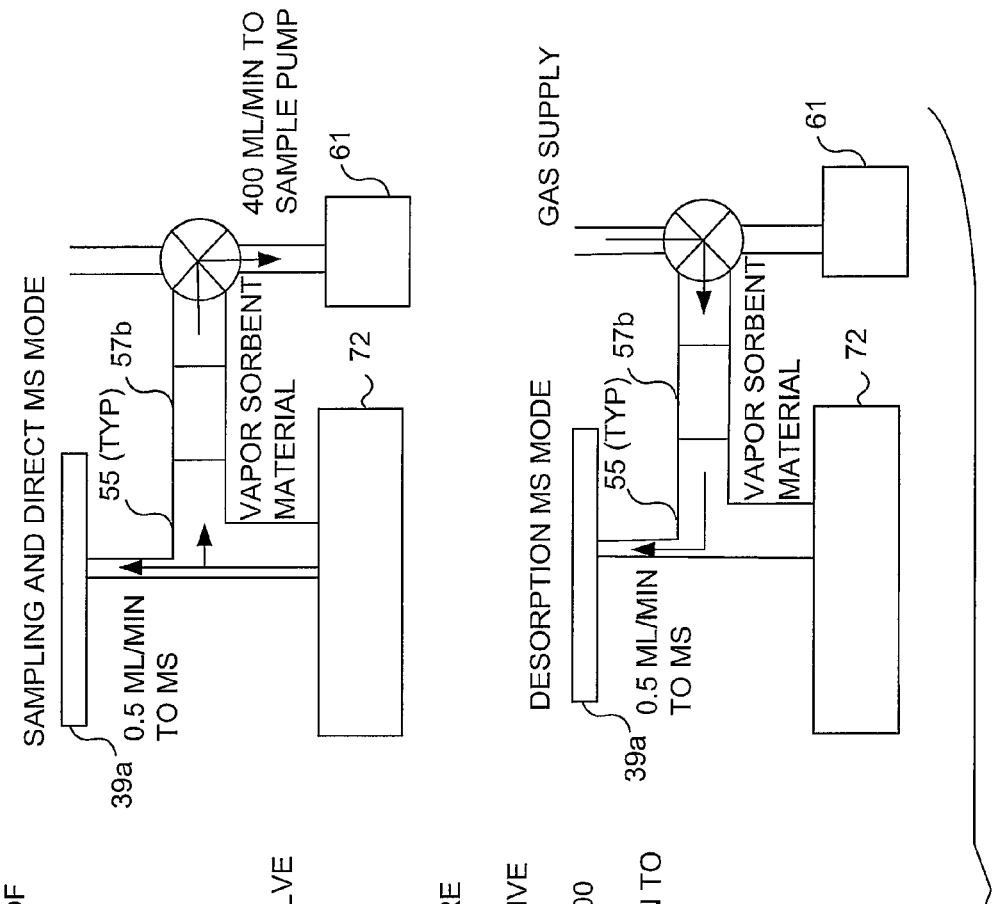
FIG. 4B is a functional block diagram providing additional detail about the vapor sampling chamber of FIG. 4A, and conveying a vapor sample to a mass spectrometer for screening of toxic chemical agents.
Figure 5A:
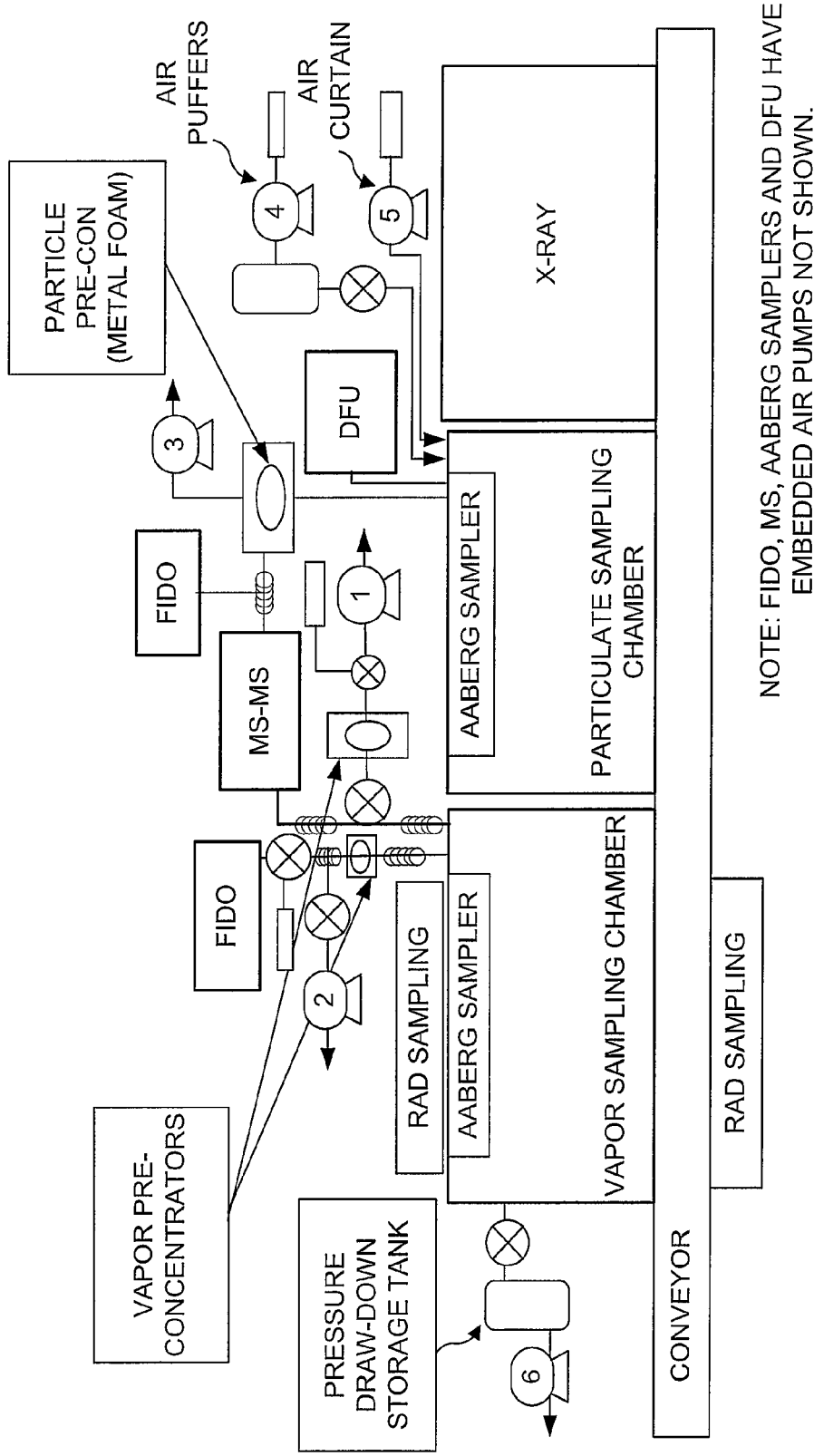
FIG. 5A is a functional block diagram of a screening system closely related to the screening system of FIG. 4A, providing additional detail about the structure of ancillary components such as pumps.
Figure 5B:
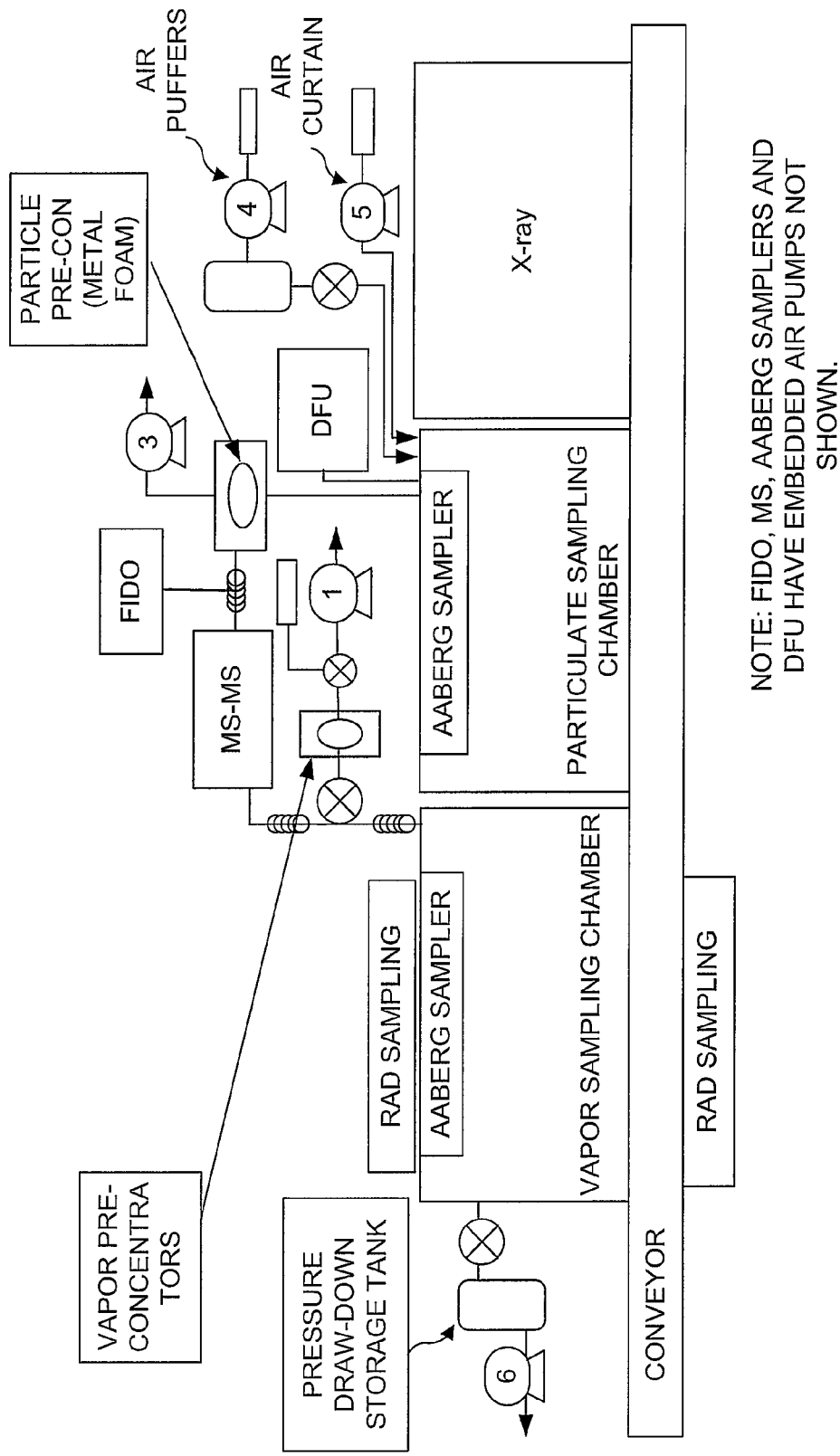
FIG. 5B is a functional block diagram of a screening system closely related to the screening system of FIG. 5B, but which employs only a single explosive detector.
Figure 6:
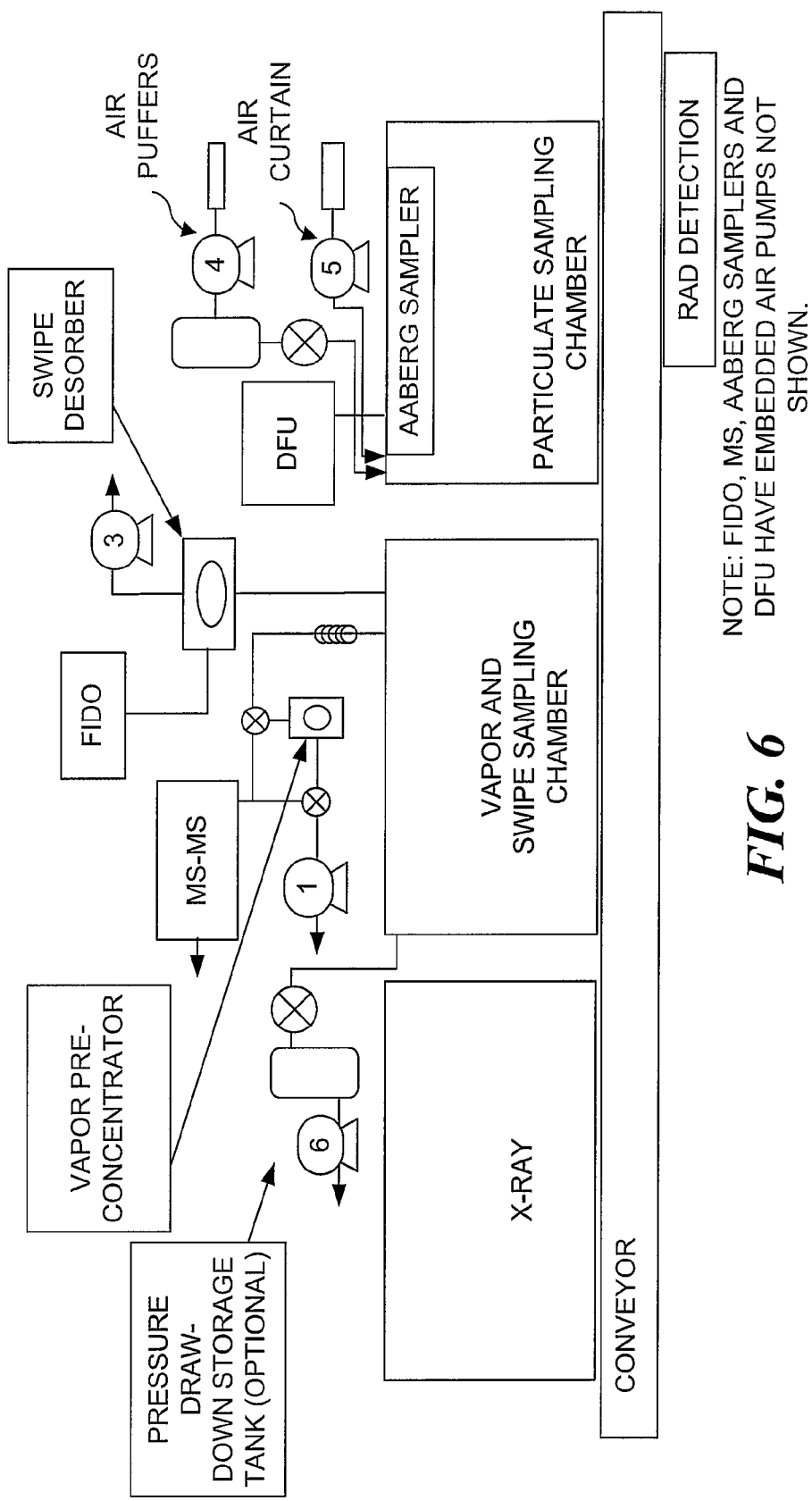
FIG. 6 is a functional block diagram of a screening system closely related to the screening system of FIG. 5B, but in which the positions of the X-ray imager and vapor sampling chamber have been reversed.

FIG. 4B provides details relating to the vapor pre-concentrators associated with vapor sampling chamber 72 in FIG. 4A. While only vapor pre-concentrator 57b is discussed in detail, it should be recognized that vapor-pre-concentrator 57a serves a similar purpose and function. In the Sampling and Direct MS Mode, vapor (i.e., a gaseous fluid) is drawn from the vapor sampling chamber into the mass spectrometer, and also through a vapor sorbent material (i.e., vapor pre-concentrator 57b). A sample pump 61 draws the vapor from the sampling chamber through fluid lines 55. Exemplary implementations of vapor pre-concentrator 57b include the use of a short gas chromatograph column (preferably with temperature control) and a packed sorbent bed (preferably with active cooling). Thus, in the Sampling and Direct MS Mode, the mass spectrometer is analyzing an ambient vapor sample, and a more concentrated vapor sample is being accumulated by the vapor pre-concentrator. In the Desorption MS Mode, an inert gas is employed to strip the concentrated vapor sample off of the vapor pre-concentrator and into the mass spectrometer for analysis of the concentrated sample. It should be recognized that the specific configuration of the structural elements in FIG. 4B is intended to be exemplary, rather than limiting. It should also be recognized that the specific flow rates noted in FIG. 4B are intended to be exemplary, rather than limiting.

FIG. 4C provides details relating to filter 63a associated with particulate sampling chamber 74 in FIG. 4A. Filter 63a is configured to collect explosive particles, and selectively heat the trapped particles to selectively vaporize the collected particles. The vaporized particles can then be directed to explosives detector 39b or mass spectrometer 39a via fluid lines 55 as desired (based on manipulating valve 51c). An exemplary filter media is a foamed nickel filter. Temperature of the filter is selectively controlled by incorporating heating elements in or around the filter or a filter holder (no specific limitation on the structural relationship of the filter, the heating element, or the filter holder is intended to be conveyed), and if desired the downstream fluid lines (preferably implemented by metal tubing, in an exemplary but not limiting embodiment). Thus, in an Accumulation Mode, the particles are trapped on the filter media. In a Desorption MS Mode, heat is applied to vaporize the particles, and a position of valve 51c determines whether the sample vapor is directed to mass spectrometer 39a or explosive detector 39b. A second explosives detector is beneficial because if the first unit is in need of maintenance or extra time to stabilize after a positive detection event, the second unit is immediately available. Thus, the second sensor allows the system to have a higher reliability and a higher throughput. However, in such a two detector embodiment, a valve will be required, which can cause loss of analyte. Thus the concepts disclosed herein also encompass the use of a single explosives detector. It should also be recognized that the specific flow rates and temperatures noted in FIG. 4C are intended to be exemplary, rather than limiting.

FIG. 4D provides details relating to filter 63*b* associated with particulate sampling chamber 74 and DFU 41*a* in FIG. 4A. Filter 63*b* is configured to collect bio-threat (or bio-warfare) particles, for later analysis (i.e., after a batch of mail or parcels have been screened). An exemplary filter media is a conventional high efficiency particulate air (HEPA) filter. It should also be recognized that the specific flow rates and vendor noted in FIG. 4C are intended to be exemplary, rather than limiting.

FIG. 5A is a functional block diagram illustrating yet another modification of system 31 (FIG. 3A). FIG. 5A is very similar to FIG. 4A, but is more detailed in that it illustrates various pumps used to the screening system. Pumps 1 and 2 enable sample laden air from the sampling chambers to be drawn through the vapor pre-concentrators, while Pump 3 enables sample laden air to be drawn through the Particle Pre-Con (metal foam). Pump 4 enables a storage volume to be filled with compressed air to be used to produce the puffs of air to dislodge particles from a parcel, while Pump 5 is configured to provide an air curtain to contain the particles in the sampling chamber. Pump 6 and the pressure pull down storage tank are configured to rapidly pull air out of the vapor sampling chamber, thereby to facilitate drawing air out of the parcel for detection. The screening system of FIG. 5A represents a modification with respect to the screening system of FIG. 4A, in that the screening system of FIG. 5A includes a specialized sample nozzle in the vapor sampling chamber and the particle sampling chamber. Specialized directional sample nozzles offer an alternative to bulk air sampling. Directional vapor sampling provides great benefits in reducing the volume of air sampled in order to collect the same number of useful particles for deposition onto the pre-concentration medium. An exemplary directional vapor sampling nozzle is a vortex nozzle. Aaberg nozzles represent another exemplary type of a directional vapor sampling nozzles, and Aaberg nozzles and vortex nozzles can be combined to achieve a Vorberg nozzle, which represents yet another exemplary type of directional sampling nozzle. Empirical studies in directional trace sampling conducted during the development of the mail screening technologies disclosed herein indicate that Aaberg nozzles can provide substantial increases in effective standoff distance and substantial reductions in sampling times. The straightforward benefits of directional suction versus simple suction devices are based in the fact that simple suction devices draw fluid from all directions equally, and consequently as the distance of the target volume of air from the input nozzle grows the volume of air that must be sampled in order to achieve capture of target vapor particles increases at a cubic rate. The relationship between the distance from the target and the increased volume of air required for sampling becomes a squared relationship. Additionally, the Aaberg nozzle increases the speed of the moving air, decreasing sample time. The use of an Aaberg nozzle will preferably be implemented along with a mechanism to move the nozzle close to the parcel.

FIG. 5B is a functional block diagram illustrating yet another modification of system 31 (FIG. 3A). As with FIG. 5A, FIG. 5B is more detailed than other previous Figures, in that it illustrates various pumps used to the screening system. The screening system of FIG. 5B represents a modification with respect to the screening system of FIG. 4A, in that the screening system of FIG. 5B includes an Aaberg nozzle (discussed above) and only a single explosive detector (although it should be noted that a second detector can be beneficially employed, as described above).

FIG. 6 is a functional block diagram illustrating yet another modification of system 31 (FIG. 3A). As with the screening system of FIG. 5B, the screening system of FIG. 6 includes an Aaberg nozzle (discussed above) and only a single explosive detector. Significantly, the screening system of FIG. 6 includes an automated sampling arm and a sampling substrate associated with the low flow detection component (i.e., the vapor sampling chamber and related detectors and sample handling equipment), such that while a vapor sample is collected for the mass spectrometer, the parcel or item of mail is swiped by the automated sample arm, such that a sample is accumulated on the sampling substrate. As discussed above, the sample substrate is then heated to vaporize any collected particles, and the vapors are conveyed to the explosives detector. Furthermore, note that the position of the X-ray imaging station has been moved relative to the earlier described screening systems. It should be noted that the relative position of the X-ray screening can be varied, so long as radiation associated with such screening does not affect other components. It should also be noted the embodiments disclosed herein include embodiments with and without Aaberg nozzles, because such technology has advantages and disadvantages. A disadvantage of the Aaberg nozzle is that it disturbs the particles and vapors. Empirical studies are being conducted to determine which approach (Aaberg nozzle or no Aaberg nozzle) provides better functionality.

FIG. 7A provides details relating to exemplary pumps that can be used with screening systems disclosed herein. It should also be recognized that the specific details noted in FIG. 7A are intended to be exemplary, rather than limiting.

FIG. 7B provides details relating to exemplary valves that can be used with screening systems disclosed herein. It should also be recognized that the specific details noted in FIG. 7B are intended to be exemplary, rather than limiting.

FIG. 7C provides details relating to exemplary timing control logic that can be used with screening systems disclosed above, based on screening system 31 of FIG. 3A (i.e., screening systems including a low flow detection component/vapor sampling chamber and a high flow detection component/particle sampling chamber). It should also be recognized that the specific details noted in FIG. 7C are intended to be exemplary, rather than limiting.

FIG. 8 is a functional block diagram of a mail screening system 71, which differs from mail screening system 31 of FIG. 3A (which can be broadly characterized as including a low flow sampling component and a high flow sampling component), in that mail screening system 71 can be broadly characterized as including an automated sampling component configured to swipe an item of mail to collect a sample. Mail screening system 71 is configured to automatically screen an item of mail for at least one threat selected from the group consisting of CBRNE threats. The system includes a detector 79 configured to analyze a sample collected by the system, where the sample is associated with the item of mail, to determine if at least one threat selected from the group consisting of CBRNE threats is associated with the item of mail. The system also includes an automated sample arm 73, means to achieve a relative motion between the automated sample arm and the item of mail (means 81); a sampling substrate 75 coupled to the automated sample arm, and means to intentionally remove the sample from the sampling substrate and convey the sample to the detector for analysis (means 77). In a particularly preferred but not limiting embodiment, detector 79 is an explosives detector. Sampling substrate 75 comprises a generally planar surface, and the automated sample arm is configured to position the sampling substrate such that the generally planar surface of the sampling substrate wipes a generally planar portion of the item of mail as the sampling substrate contacts the item of mail while there is relative motion between the automated sample arm and the item of mail. In an exemplary (but not limiting) embodiment, means 81 achieves the relative motion by both moving the item of mail relative to the automated sample arm (in an exemplary but not limiting embodiment a conveyor belt is used to move parcels or items of mail through the screening system, which in many variations will also include other screening stations in addition to the swiping station with the automated sample arm), and by moving the automated sample arm relative to the parcel (for example, in a particularly preferred but not limiting embodiment, a sizing component such as described above determines a position of a parcel on the conveyor belt, and the automated sample arm moves the sampling substrate such that the sampling substrate is wiped across the parcel). In an exemplary (but not limiting) embodiment, means 77 intentionally removes the sample on the sample substrate by heating the sample substrate to volatilize the sample. The sample vapor is then conveyed to the detector. In some embodiments, the detector is disposed immediately adjacent to the sampling substrate as it is heated, and the vapors move directly into the detector. In other embodiments, means 77 includes some structure (such as fluid lines and a sampling nozzle, if desired) to convey the sample vapor from the location where the sample substrate is heated to the detector.

FIG. 9 illustrates various exemplary embodiments 130 of automated sample arms. Each such embodiment is configured to be employed in a screening system where the item of mail (a parcel in an exemplary embodiment, although it should be recognized that a swipe sample could be to taken of the upper surface of a letter or flat) is moved through the system on a conveyor (such as a conveyor belt or a roller conveyor). A sizing component (such as a light curtain) is used to determine at least one dimension of the item of mail (such as its height), so that the automated sample arm can be positioned properly relative to the item of mail, so that the sample substrate can be wiped across a surface of the item of mail. Each of the embodiments 130 includes a frame configured to support the automated sample arm. In the illustrated embodiments, the conveyor component passes through the frame, although it should be recognized that such a configuration is simply exemplary, and not limiting on the actual structure employed. Where the conveyor component passes through the frame, the frame must be large enough to accommodate the largest parcel size likely to be encountered.

An embodiment 130*a* is configured to move a sample substrate 87 along a single linear axis (indicated by an arrow 89*a*), via translation means 89. It should be recognized that translation means 89 can be implemented in many ways. Exemplary, but not limiting translation means include hydraulics, pneumatics, worm drives, screw drives, chain drives, and combinations of racks gears and pinions. Translation means 89 uses data from a sizing component (such as a light curtain) to position sampling substrate 87 so that the sampling substrate swipes (or scans) a line across a top surface of parcel 91 as conveyor 32 moves parcel 91 along an axis indicated by an arrow 83*a*. In other words, translation means 89 adjusts a height of the sampling substrate relative to a height of the parcel. It should be noted that the sample substrate could be replaced with a sample nozzle, such that translation means 89 moves the sample nozzle close to but not in contact with the upper surface of parcel 91 (such a substitution could be performed for each of the following embodiments as well).

An embodiment 130*b* is configured to move sample substrate 87 along two different linear axes (indicated by arrow 89*a* and an arrow 93*a*), via translation means 89 and a translation means 93. Again, each translation means can be implemented using many different structures. As noted above, translation means 89 uses data from a sizing component (such as a light curtain) to position sampling substrate 87 so that the sample substrate swipes (or scans) a line across a top surface of parcel 91 as conveyor 32 moves parcel 91 along an axis indicated by an arrow 83*b*. Translation means 93 can be used to move the sample substrate to a different position on the upper surface of the parcel. The combined motions of the conveyor and translation means 93 enable diagonal scans or swipes to be achieved. If translation means 93 is moving rapidly relative to the motion of the parcel caused by conveyor 32 (the parcel motion is indicated by an arrow 83*b*), then a plurality of diagonal scans or swipes across the surface of the parcel can be achieved. To avoid allowing translation means 93 to move the sample substrate beyond the surface of the parcel during scanning/swiping, translation means 93 can use data from a sizing component (such as a light curtain). Note that navigation of the top of the parcel by the sampling substrate requires coordination of motion of the automated sample arm and the conveyor.

An embodiment 130*c* is configured to move sample substrate 87 along three different linear axes (indicated by arrow 89*a*, arrow 93*a*, and an arrow 95*a*), via translation means 89, translation means 93, and one or more translation means 95. Again, each translation means can be implemented using many different structures. Translation means 89 and 93 function as described above. Translation means 95 can be used to move the sample substrate to a different position on the upper surface of the parcel. Note that translation means 95 enables motion in a direction orthogonal to the motion enabled by translation means 93. With parcel 91 in a static position, the combined motions of translation means 93 and 95 enable diagonal scans or swipes, or raster scanning/swiping to be achieved (even spiral scanning can be achieved if desired). If translation means 93 is moving rapidly relative to the motion of translation means 95 (or vice versa), then a plurality of diagonal scans or swipes across the surface of the parcel can be achieved. To avoid allowing translation means 95 to move the sample substrate beyond the surface of the parcel during scanning/swiping, translation means 95 can use data from a sizing component (such as a light curtain). Note that navigation of the top of the parcel by the sampling substrate can be achieved independent of the motion of the conveyor.

An embodiment 130*d* is configured to move sample substrate 87 along three different linear axes (indicated by arrow 89*a*, arrow 93*a*, and arrow 95*a*) and two rotational axes, via translation means 89, translation means 93, (one or more of) translation means 95, and rotational means 97 and 99. Each translation means and rotational means can be implemented using many different structures. Translation means 89, 93 and 95 function as described above. Rotational means 97 can be coordinated with translation means 89 and 95 to enable sides 91*a* and 91*b* to be scanned/swiped. Rotational means 99 can be coordinated with translation means 89 and 93 to enable a side 91*c* to be scanned/swiped. If an additional translation means 93 is added to portion 101 of the frame, then rotational means 99 can be coordinated with translation means 89 and additional translation means 93 to enable a side 91*d* to be scanned/swiped. Note that navigation of the top and sides of the parcel by the sampling substrate can be achieved independent of the motion of the conveyor. Further note that the dimensions of the frame have been increased to accommodate the degrees of freedom required by the rotational means.

With respect to FIG. 9, it should be understood that all dimensions are intended to be exemplary, and not limiting.

FIG. 10 is a functional block diagram of yet another screening system 34 disclosed herein, while FIG. 11 is an artist's representation of screening system 34. Screening system 34 includes a plurality of screening stations, including (from left to right in FIG. 11) a tag reading station 28, a radiation screening station 22, a parcel dimension screening station 24, an automated sample arm screening station 36 (generally consistent with the component described in connection with FIG. 8), a combined toxic chemical and bio-warfare screening station 26, and an X-Ray imaging screening station 20. Conveyor 32 moves parcels through the screening system, and controller 30 (not shown in FIG. 11) collects the data from each parcel screened and controls the screening process. Tag reading station 28 can be implemented with RFID readers or optical code readers, depending on the tag technologies selected.

Parcel dimension screening station 24 can be implemented using a light curtain, which determines the dimensions of the parcel, and the parcel's relative position on the conveyor. As discussed above (particularly with respect to FIG. 8), the parcel dimension data is used by automated sample arm screening station 36 to properly position a sampling substrate relative to the parcel passing through the automated sample arm screening station, so that the sample substrate is swiped across one or more surfaces of the parcel to collect a sample. In an exemplary embodiment, automated sample arm screening station 36 includes heat elements to vaporize a sample collected on the sampling substrate, and an explosives detector, generally as discussed above. It should be recognized however, that the concepts disclosed herein encompass other embodiments, such as an automated sample arm with a nozzle configured to collect a vapor sample, so that the automated sample arm does not touch the parcel, as well as embodiments where the detector is a mass spectrometer (i.e., a toxic chemical detector) rather than an explosives detector (or both a mass spectrometer and an explosives detector). In some embodiments the conveyor is halted to keep the parcel motionless while the automated sample arm is collecting a sample. In other embodiments the automated sample arm and the parcel move at the same time.

In at least one embodiment, automated sample arm screening station 36 includes means to regenerate the sample substrate so that it can be re-used. In some embodiments, a plurality of substrates are provided initially, and after a sample is collected and a portion is volatilized, the used sample substrate is moved to a regenerator (generally a heated chamber that can heat the sampling substrate for a period of time likely to be sufficient to remove substantially all traces of the sample). A fresh sample substrate is used to collect the next sample. After the initial sample substrates have all been used, a regenerated sample substrate is employed. The number of sample substrates required is a function of the speed at which samples are collected and the time required to regenerate the sample substrates (faster sampling rates and slower regeneration times will require larger numbers of sample substrates). If the regenerated sample substrate needs to be cooled before re-use, either more sample substrate will need to be provided initially, or cooling means must be provided. Empirical studies indicate that regeneration is effective for up to 100 samples. Alternatively, a new sample substrate can be used for each sample.

Combined toxic chemical and bio-warfare screening station 26 includes a housing having an entry and exit. The interior of the housing is separated from the ambient atmosphere by air curtains 38 (see FIG. 11). While inside the housing, two different samples are collected. One such sample is a vapor sample, which is collected and conveyed to a mass spectrometer to determine if a toxic chemical agent is associated with the parcel/item of mail. Acquisition and conveyance of vapor samples to a mass spectrometer have been discussed in detail above, and similar techniques can be used by combined toxic chemical and bio-warfare screening station 26. A second sample collected is a bio-threat or bio-warfare sample, which is collected by a DFU generally as discussed above. If a puffer is used to collect the bio-threat sample, preferably the toxic chemical sample is collected first, so that the puffer does not disperse trace vapors before they can be collected. The vapor sample is analyzed by the mass spectrometer, and the bio-threat sample is not analyzed until a batch of mail has been processed (although it should be recognized that a real time bio-threat detector can be employed if desired). In an exemplary, but not limiting embodiment, conveyance of a parcel from one station to the next is completed in one to two seconds, and sampling is completed 5-25 seconds; thus parcels briefly stop at each station.

The parcel is then moved through the X-ray imaging screening station. As discussed in detail above, a trained operator can be used to review the image for each parcel, the images can be screened automatically by an expert system, or the images can be stored and reviewed only if the explosives detector indicates the presence of an explosive agent.

In FIG. 11, note that a batch 40 of five parcels has been set aside. Generally, such batches of parcels are stored until the bio-threat sample collected by a DFU (or by a similar sampler) is analyzed. If no bio-threat is found, the batch is released for delivery. If a bio-threat is found, the parcels must be examined to determine the parcel or parcels associated with the threat. It should also be recognized that such batching can be beneficial if one of the detection technologies being utilized requires more analysis time than is available while the parcel is moving through the system. Similarly, if all detection technologies employed in the screening system are sufficiently rapid, then batching may not be required at all.

FIG. 12 is a flow chart illustrating exemplary method steps for using screening system 34 (FIGS. 10 and 11). In a step 90, the method begins when a parcel (or other item of mail) is loaded onto the conveyor. In a step 92 the label (RFID or optical bar code) of the parcel is read. In a step 94, the radiation screening is performed. In a step 96 at least one dimension of the item of mail is sampled, for example, by light curtain 24 (see FIG. 11). This measurement is useful in ensuring that the sampling substrate can be properly positioned to swipe a sample from one or more surfaces of the parcel, as indicated by a step 98. In a step 100, the sample is intentionally removed from the substrate (in an exemplary embodiment, the sampling substrate is heated to volatilize at least a portion of the sample). In a step 102 the sample substrate is regenerated to prepare for the acquisition of another sample from another parcel (or from the same parcel, if the system is configured to obtain more than one sample). As noted above, the concepts disclosed herein encompass many variations, including the use of an automated sample arm to move a sampling nozzle over a surface of the parcel, as opposed to swiping the parcel to collect a solid sample (thus, the removing and regenerating step would not be required). The volatilized sample is then conveyed to an explosive detector and analyzed, as indicated in a step 104.

Then the parcel moves to the next sampling station (combined toxic and BW screening station 26), and a vapor sample is collected (as indicated by a step 106), and analyzed by a mass spectrometer to determine if a toxic chemical agent is present (as indicated in a step 108). While the parcel is in the combined screening station, a bio-threat sample is acquired by the DFU (note this step may involve the use of a puffer to drive particles off of the parcel), as indicated in a step 110. The parcel in then moved to the X-ray screening station, and an X-ray image is taken, as indicated by a step 112.

In a decision step 114, a determination is made as to whether the radiation detector, the explosive detector, the toxic chemical detector or the X-ray image has identified a threat agent. If so, secondary screening can be initiated if desired, as indicated in step 126. Such secondary screening can involve the collection and analysis of another sample from the parcel, analysis of a collected sample using an additional detection technology, or identification of the source of radiation detection by a radiation detector that simply responds to the presence of radiation, without identifying the source. Based on the type of threat detected, appropriate responses can be executed.

If no threat is detected, then in decision step 116 a determination is made as to whether each item of mail (or parcel) in a batch of mail has been screened. If not, then the screening process is repeated for the next parcel, as indicated in a step 118. If each parcel in a batch has been screened, then the DFU sample is analyzed for bio-agents/bio-warfare agents, as indicated in a step 120. If in a decision step 122 it is determined that no BW agent is present, the batch of parcels is released for delivery, as indicated in a step 124. If in a decision step 122 it is determined that a BW agent is present, secondary screening on the batch of parcels is performed (as indicated in step 126), in order to identify one or more parcels associated with the detected BW threat. Appropriate responses can then be implemented to counter the threat.

It should be recognized that the steps disclosed with respect to FIG. 12 are intended to be exemplary, and not limiting.

Where specific dimensions are referred to above, it should be recognized that the disclosure is merely intended to be exemplary, and it is further intended to be broadly interpreted so as to encompass variations to such specifically identified parameters. Thus, such parameters should not be considered to be limiting, unless limitations are specifically recited in the claims that follow.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A system for automatically screening an item of mail for the presence of at least two different types of threat agents selected from a group consisting of a radiological agent, a toxic chemical agent, a bio-threat agent, and an explosive agent, the system including:
   (a) an explosive detection component that determines if an explosive agent is associated with the item of mail, the explosive detection component comprising:
      (i) an automated sampling arm that automatically places a sampling medium in physical contact with at least one surface of the item of mail; and
      (ii) means to analyze the sample collected by the sampling medium; and
   (b) at least one additional detection component selected from a group of detection components consisting of:
      (i) a radiation detection component, the radiation detection component detecting if radiation is associated with the item of mail;
      (ii) a toxic chemical detection component, the toxic chemical detection component determining if a toxic chemical agent is associated with the item of mail; and
      (iii) a bio-threat sampling component, the bio-threat sampling component collecting a bio-threat sample to be analyzed to determine if a bio-threat agent is disposed on a surface of the item of mail.

2. The system of claim 1, wherein the system includes at least two of the additional detection components identified in claim 1.

3. The system of claim 1, wherein the bio-threat sampling component is puffer-based, the puffer-based bio-threat sampling component collecting the bio-threat sample using at least one technique selected from a group consisting of:
   (a) filtering a gaseous fluid used to dislodge bio-threat particles associated with the item of mail;
   (b) employing a direct-to-liquid sample collector; and
   (c) employing a real-time sensor configured to trigger a sample collector to obtain a sample suitable for automated bio-threat analysis.

4. The system of claim 1, further comprising an X-ray based imager, the X-ray based imager being configured to image an internal content of the item of mail, the X-ray based imager being spaced apart from the radiation detection component so as to minimize interference between the X-ray based imager and the radiation detection component, the X-ray based imager comprising at least one element selected from the group consisting of:
   (a) a two-dimensional X-ray imager;
   (b) a backscatter X-ray imager;
   (c) a two-power X-ray imager; and
   (d) a three-dimensional X-ray imager.

5. The system of claim 1, wherein the toxic chemical detection component comprises a toxic chemical agent sampling component, the toxic chemical agent sampling component being configured to collect a chemical sample to be analyzed to determine if a toxic chemical agent is associated with the item of mail.

6. The system of claim 1, further comprising a bio-threat detection component, the bio-threat detection component being configured to analyze the bio-threat sample to determine if a bio-threat agent is associated with the item of mail.

7. A system for automatically screening mail for hazardous threats in an item of mail, the system comprising:
   (a) a relatively low flow sampling component, the relatively low flow sampling component automatically collecting a vapor sample from the item of mail; and
   (b) means to analyze the vapor sample collected by the relatively low flow sampling component, to determine if at least one contaminant is associated with the item of mail, the at least one contaminant being selected from a group of contaminants consisting of:
      (i) a toxic chemical agent; and
      (ii) an explosive agent; and
   (c) a relatively high flow sampling component, the relatively high flow sampling component automatically collecting a particle sample from the item of mail, the particle sample having been dislodged from the item of mail by a fluid directed toward the item of mail by the relatively high flow sampling component, the system being configured such that the item of mail passes through the relatively low flow sampling component before passing through the relatively high flow sampling component, such that the relatively high flow sampling component does not disrupt the collection of the vapor sample.

8. The system of claim 7, further comprising means to analyze the particle sample collected by the relatively high flow sampling component, to determine if a bio-threat agent is associated with at least one element selected from a group consisting of the item of mail and a batch of mail containing the item of mail.

9. The system of claim 7, further comprising a sizing component configured to determine at least one dimension of the item of mail, the sizing component being disposed such that the item of mail is measured before the item of mail is sampled by the relatively low flow sampling component, so that a measurement of the item of mail provided by the sizing component can be used to ensure that an automated nozzle arm is properly positioned relative to the item of mail, so that a sampling nozzle portion of the automated nozzle arm is disposed adjacent to a surface of the item of mail to acquire the vapor sample.

10. The system of claim 7, further comprising a wipe sampling component, wherein the wipe sampling component comprises:
    (a) an automated sample arm;
    (b) means to achieve a relative motion between the automated sample arm and the item of mail;
    (c) a sampling substrate coupled to the automated sample arm, the sampling substrate collecting the sample as the sampling substrate contacts a portion of the item of mail while there is relative motion between the automated sample arm and the item of mail, the sampling substrate being configured to retain the sample until the sample is intentionally removed; and
    (d) means to intentionally remove the sample from the sampling substrate and convey the sample to an explosive detector for analysis.

11. The system of claim 10, wherein said means to convey the sample to the explosive detector comprises a desorber configured to heat the sampling substrate, in order to vaporize particulates collected by the sampling substrate, such that the vapors are directed to the explosive detector.

12. The system of claim 10, further comprising a sizing component configured to determine at least one dimension of the item of mail, the sizing component being disposed such that the item of mail is measured before the item of mail is sampled by the automated sample arm, so that a measurement of the item of mail provided by the sizing component can be used to ensure that the automated sample arm is properly positioned relative to the item of mail, so that the sampling substrate contacts the item of mail to acquire the sample.

13. A mail screening system configured to automatically screen an item of mail for at least one threat selected from the group consisting of Chemical, Biological, Radiological, Nuclear and Explosive (CBRNE) threats in an item of mail, the system comprising:
    (a) a detector configured to analyze a sample collected by the system, the sample being associated with the item of mail, to determine if at least one threat selected from the group consisting of CBRNE threats is associated with the item of mail;
    (b) an automated sample arm configured to be selectively positionable about a plurality of different axes;
    (c) means to achieve a relative motion between the automated sample arm and the item of mail;
    (d) a sampling substrate coupled to the selectively positionable automated sample arm, the selectively positional automated sample arm enabling the sampling substrate to collect the sample from at least two non-contiguous surfaces of the item of mail while there is relative motion between the automated sample arm and the item of mail, the sampling substrate being configured to retain the sample until the sample is intentionally removed; and
    (e) means to intentionally remove the sample from the sampling substrate and convey the sample to the explosive detector for analysis.

14. The system of claim 13, wherein the sampling substrate comprises a generally planar surface, and the automated sample arm is configured to position the sampling substrate such that the generally planar surface of the sampling substrate wipes a generally planar portion of the item of mail as the sampling substrate contacts the item of mail while there is relative motion between the automated sample arm and the item of mail.

15. The system of claim 13, wherein said means to intentionally remove the sample from the sampling substrate comprises a desorber configured to heat the sampling substrate, in order to vaporize low-volatility chemicals collected by the sampling substrate, such that the vapors are conveyed with a carrier gas to the detector.

16. The system of claim 13, further comprising a light curtain configured to determine at least one dimension of the item of mail, the light curtain being disposed such that the item of mail is measured before the item of mail is sampled by the automated sample arm, so that a measurement of the item of mail provided by the light curtain can be used to ensure that the automated sample arm is properly positioned relative to the item of mail, so that the sampling substrate contacts the item of mail to acquire the sample.

17. The system of claim 13, further comprising:
    (a) a relatively low flow sampling component, the relatively low flow sampling component being configured to detect if a toxic chemical agent is associated with the item of mail, the relatively low flow sampling component including a mass spectrometer configured to continuously monitor air proximate the relatively low flow sampling component; and
    (b) a relatively high flow sampling component, the relatively high flow sampling component being configured to automatically collect a bio-threat sample to be analyzed to determine if a bio-threat agent is associated with at least one element selected from a group consisting of the item of mail and a batch of mail containing the item of mail, the relatively high flow sampling component collecting the bio-threat sample by filtering at least one element selected from a group consisting of air proximate the item of mail and a gaseous fluid used to dislodge bio-threat particles associated with the item of mail, the system being configured such that the item of mail passes by the automated sample arm and the relatively low flow sampling component before passing by the relatively high flow sampling component.

18. A method for automatically screening an item of mail for at least one threat selected from the group consisting of Chemical, Biological, Radiological, Nuclear and Explosive (CBRNE) threats, the method comprising the steps of:
    (a) positioning a sampling substrate such that the sampling substrate is in contact with at least a portion of the item of mail, using an automated sampling arm;
    (b) achieving a relative motion between the sampling substrate and the item of mail, thereby collecting the sample on the sampling substrate, such that the sample is retained upon the sampling substrate until the sample is intentionally removed;

(c) intentionally removing the sample from the sampling substrate and conveying the sample to a detector configured to analyze the sample; and (d) analyzing the sample with the detector to determine if at least one threat selected from the group consisting of CBRNE threats is associated with the item of mail.

19. The method of claim 18, wherein the sampling substrate is substantially planar, and the step of positioning the sampling substrate comprises the step of placing the substantially planar sampling substrate in contact with a planar surface of the item of mail.

20. The method of claim 18, wherein the step of intentionally removing the sample from the sampling substrate and conveying the sample to the detector comprises the steps of:

(a) using heat to volatilize at least a portion of the sample retained on the sampling substrate; and (b) directing the volatilized sample to the detector.

21. The method of claim 18, further comprising the step of regenerating the sampling substrate for future use by heating the sampling substrate for a period of time sufficient to remove substantially all remaining traces of the sample from the sampling substrate.

22. The method of claim 18, wherein the step of achieving the relative motion between the sampling substrate and the item of mail comprises the step of moving the item of mail while keeping the position of the sampling substrate relatively fixed during sampling.

23. The method of claim 18, wherein the step of achieving the relative motion between the sampling substrate and the item of mail comprises the step of moving the sampling substrate over at least one surface of the item of mail.

24. The method of claim 18, further comprising the step of determining at least one dimension of the item of mail before sampling, to facilitate properly positioning the sampling substrate relative to the item of mail.

25. The method of claim 18, wherein the step of analyzing the sample with the detector comprises the step of determining if an explosive threat is associated with the item of mail, and further comprising the step of performing secondary screening to determine if an explosive agent is in the item of mail, where the secondary screening is based on X-ray imaging.

26. The method of claim 18, wherein after the sample has been collected on the sampling substrate, further comprising the step of collecting a particulate based sample from the item of mail, the step of collecting the particulate based sample comprising the steps of:

(a) directing a jet of gaseous fluid over at least a portion of the item of mail, to dislodge any particles retained thereon; and (b) filtering an ambient gaseous environment proximate the item of mail to remove particles entrained in the gaseous environment, thereby obtaining the particle-based sample.

27. The method of claim 18, further comprising the steps of:

(a) collecting a vapor based sample from an ambient gaseous environment proximate the item of mail; and (b) analyzing the vapor based sample to detect a chemical threat associated with the item of mail.

28. A method for automatically screening an item of mail for Chemical, Biological, Radiological, Nuclear and Explosive (CBRNE) threats, the method comprising the steps of:

(a) automatically scanning the item of mail using a radiation detector that does not require obtaining a physical sample from the item of mail, to screen for radiological and nuclear threats;

(b) automatically screening the item of mail for an explosive threat by collecting a sample from the item of mail by wiping at least one surface of the item of mail using a sampling substrate that retains an explosive sample thereon until the explosive sample is intentionally removed, the sampling substrate being wiped on the at least one surface of the item of mail by an automated sampling arm, heating the sampling substrate to volatilize at least a portion of the explosive sample, and directing the volatilized explosive sample to an explosive detector;

(c) automatically collecting a vapor based sample from an ambient gaseous environment proximate the item of mail and analyzing the vapor based sample to detect a chemical threat associated with the item of mail; and (d) automatically directing a jet of gaseous fluid over at least a portion of the item of mail after collecting the vapor based sample, to dislodge any particles retained on the item of mail, and filtering an ambient gaseous environment proximate the item of mail to remove particles entrained in the gaseous environment, thereby obtaining the particle based sample that can be tested for a biological threat.

29. The method of claim 28, wherein the step of automatically screening the item of mail for an explosive threat further comprises the step of determining at least one dimension of the item of mail before sampling, to facilitate properly positioning the sampling substrate relative to the item of mail.

\* \* \* \* \*